United States Patent
Overstreet et al.

(10) Patent No.: US 11,389,621 B2
(45) Date of Patent: Jul. 19, 2022

(54) CATHETER ANCHOR SYSTEM AND METHOD THEREOF

(71) Applicant: TENSION SQUARE, LLC, Sarasota, FL (US)

(72) Inventors: Mychael Arnell Overstreet, Sarasota, FL (US); Sonya Yvonne Overstreet, Harker Heights, TX (US)

(73) Assignee: TENSION SQUARE, LLC, Sarasota, FL (US)

( * ) Notice: Subject to any disclaimer, the term of this patent is extended or adjusted under 35 U.S.C. 154(b) by 0 days.

(21) Appl. No.: 16/840,398

(22) Filed: Apr. 5, 2020

(65) Prior Publication Data
US 2020/0297976 A1    Sep. 24, 2020

Related U.S. Application Data

(63) Continuation-in-part of application No. 16/027,300, filed on Jul. 4, 2018, now Pat. No. 11,033,717.
(Continued)

(51) Int. Cl.
*A61M 25/02* (2006.01)
*B33Y 80/00* (2015.01)

(52) U.S. Cl.
CPC ..... *A61M 25/02* (2013.01); *A61M 2025/0266* (2013.01); *A61M 2025/0286* (2013.01); *B33Y 80/00* (2014.12)

(58) Field of Classification Search
CPC .... A61M 2025/024; A61M 2025/0253; A61M 2025/028; A61M 2025/0266
See application file for complete search history.

(56) References Cited

U.S. PATENT DOCUMENTS

| 4,838,878 A | 6/1989 | Kalt et al. |
| 5,163,914 A | 11/1992 | Abel |

(Continued)

FOREIGN PATENT DOCUMENTS

EP    1698368 A1 *   9/2006   ............ A61M 25/02

OTHER PUBLICATIONS

Talreja et al., Endoluminal dilatation for embedded hemodialysis catheters: A case-control study of factors associated with embedding and clinical outcomes, PLoS One. Mar. 27, 2017, vol. 12, No. 3, pp. 1-8.
(Continued)

*Primary Examiner* — Bhisma Mehta
*Assistant Examiner* — John J Crawford
(74) *Attorney, Agent, or Firm* — The Roy Gross Law Firm, LLC; Roy Gross

(57) ABSTRACT

A method and system of and for securing a lumen or catheter, after placement in a patient, to prevent unwanted removal or dislodgement of the lumen or catheter caused by patient movement and/or further medical interventions such as cardiopulmonary chest compressions, electrical defibrillation, surgical procedures, and the like. The method and system comprising simple and sterile materials that preclude the use of excessive suturing and ineffective ad-hoc methods with tape and gauze. The catheter is secured by a rubber on plastic frictional force and will resist external forces while preventing the tube structure from bending and subsequent occlusion. The device can be comfortably attached to the patient in all of the anatomical locations typically targeted for large catheter installment. The method of securement is rapid and requires only a single personnel to handle the device and the catheter tube simultaneously.

17 Claims, 32 Drawing Sheets

Related U.S. Application Data

(60) Provisional application No. 62/543,428, filed on Aug. 10, 2017.

(56) References Cited

U.S. PATENT DOCUMENTS

| | | | |
|---|---|---|---|
| 5,215,532 A | 6/1993 | Atkinson | |
| 5,292,312 A | 3/1994 | Delk et al. | |
| 5,354,283 A | 10/1994 | Bark et al. | |
| 5,395,344 A | 3/1995 | Beisang, III et al. | |
| 5,800,402 A | 9/1998 | Bierman | |
| 6,132,399 A | 10/2000 | Shultz | |
| 6,213,979 B1 | 4/2001 | Bierman | |
| 6,387,076 B1 * | 5/2002 | Landuyt | A61M 25/02 128/DIG. 6 |
| 6,569,121 B1 | 5/2003 | Purow et al. | |
| 6,770,055 B2 * | 8/2004 | Bierman | A61M 25/02 128/877 |
| 7,749,199 B2 | 7/2010 | Mogg | |
| 8,251,957 B2 | 8/2012 | Kyvik et al. | |
| 9,248,259 B2 | 2/2016 | Kyvik et al. | |
| 9,386,824 B1 | 7/2016 | Schultz | |
| 9,486,613 B2 | 11/2016 | Dickert et al. | |
| 10,086,168 B2 | 10/2018 | Olson | |
| 10,799,679 B2 * | 10/2020 | Roberts | A61M 25/02 |
| 2005/0192540 A1 * | 9/2005 | Kessler | A61M 25/02 604/180 |
| 2006/0276752 A1 * | 12/2006 | Bierman | A61M 25/02 604/174 |
| 2007/0249980 A1 | 10/2007 | Carrez et al. | |
| 2008/0200880 A1 | 8/2008 | Kyvik et al. | |
| 2010/0106114 A1 | 4/2010 | Weston et al. | |
| 2012/0245529 A1 | 9/2012 | Hummen et al. | |
| 2012/0271240 A1 * | 10/2012 | Andino | A61M 25/02 604/180 |
| 2012/0330255 A1 | 12/2012 | Carlin | |
| 2014/0207072 A1 | 7/2014 | Nokes, Jr. et al. | |
| 2015/0119808 A1 | 4/2015 | Khalaj | |
| 2015/0367102 A1 | 12/2015 | Andino et al. | |
| 2016/0114103 A1 * | 4/2016 | Burke | A61M 5/1418 604/179 |
| 2016/0114135 A1 | 4/2016 | Jaouani | |
| 2016/0367789 A1 * | 12/2016 | Beran | A61M 25/02 |
| 2017/0156812 A1 * | 6/2017 | Nazari | A61F 13/10 |
| 2020/0038631 A1 | 2/2020 | O'Sullivan et al. | |
| 2021/0052856 A1 * | 2/2021 | Bourang | A61M 25/02 |

OTHER PUBLICATIONS

Burying the Peritoneal Dialysis Catheter, Mitch Medical Healthcare » Laparoscopic Urology, accessed on Dec. 4, 2018, Retrieved from <https://www.mitchmedical.us/laparoscopic-urology/burying-the-peritoneal-dialysis-catheter.html>.

Maritz et al., A novel way to secure a chest drain, Ann R Coll Surg Engl. Jan. 2014, vol. 96, No. 1, p. 82.

* cited by examiner

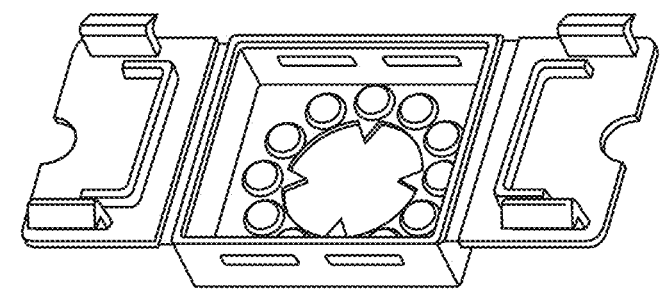
1700   FIG. 17A
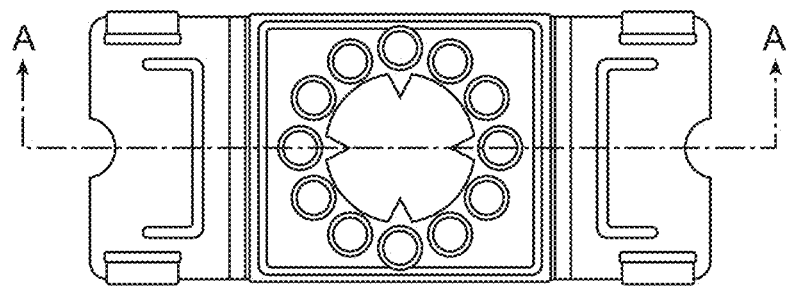
1700   FIG. 17B
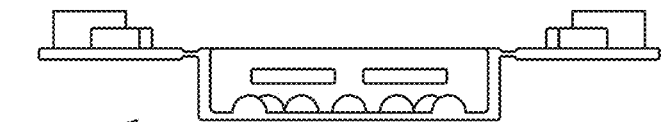
SECTION A-A
1700   FIG. 17C
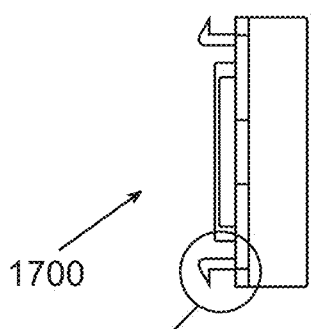
1700
DETAIL A
FIG. 17D
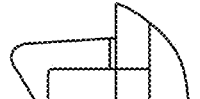
DETAIL A
FIG. 17E

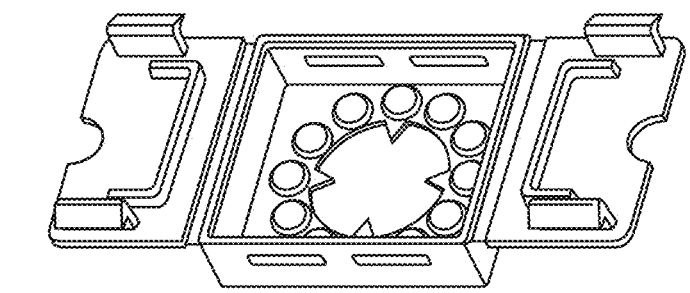
1800    FIG. 18A
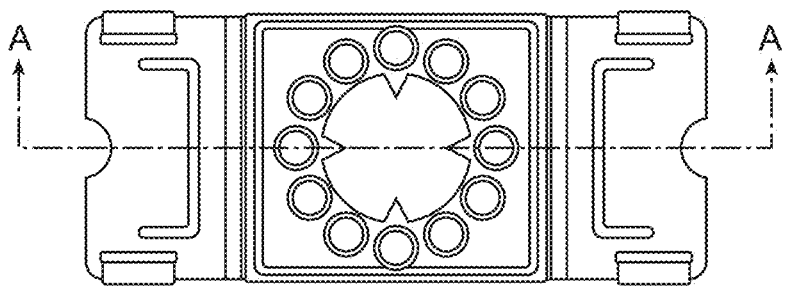
1800    FIG. 18B
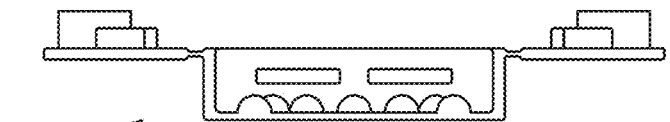
SECTION A-A
1800    FIG. 18C
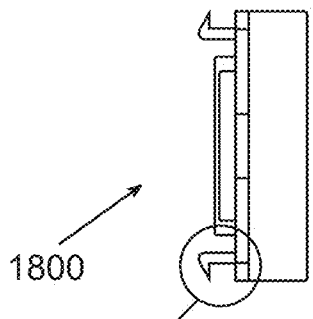
1800
DETAIL A
FIG. 18D
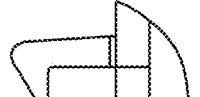
DETAIL A
FIG. 18E

SECTION A-A

DETAIL A

DETAIL A

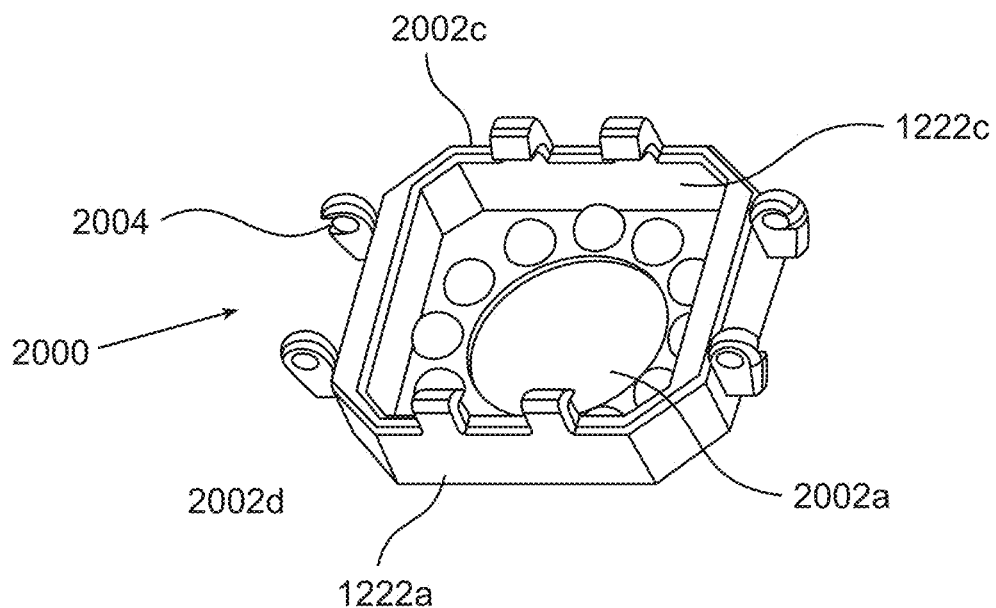
FIG. 20A
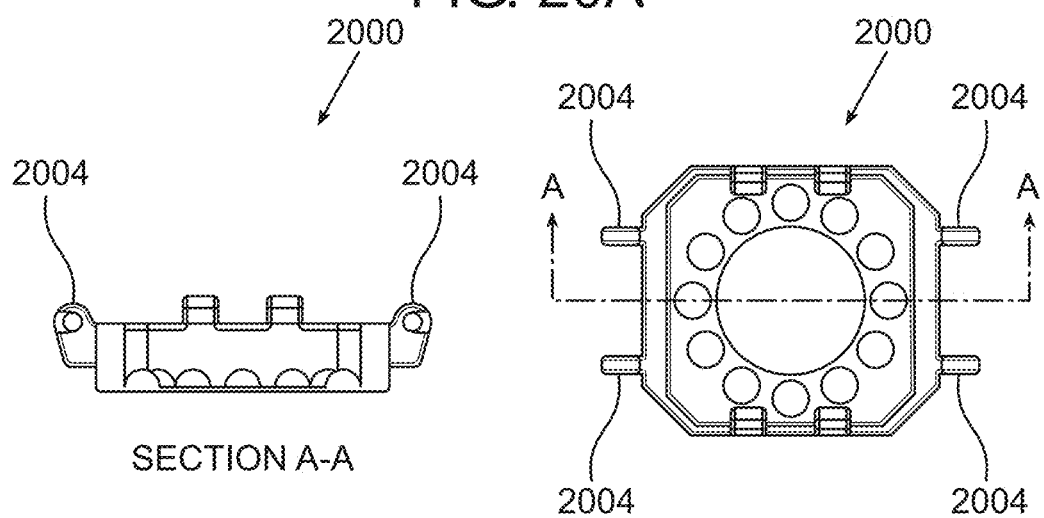
FIG. 20C
FIG. 20B
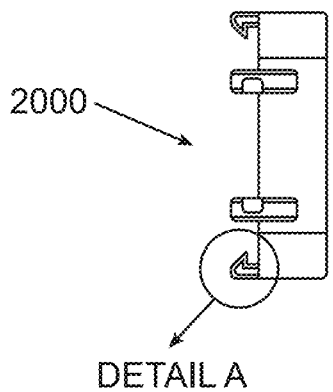
FIG. 20D
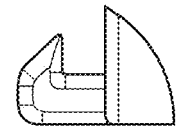
DETAIL A
FIG. 20E

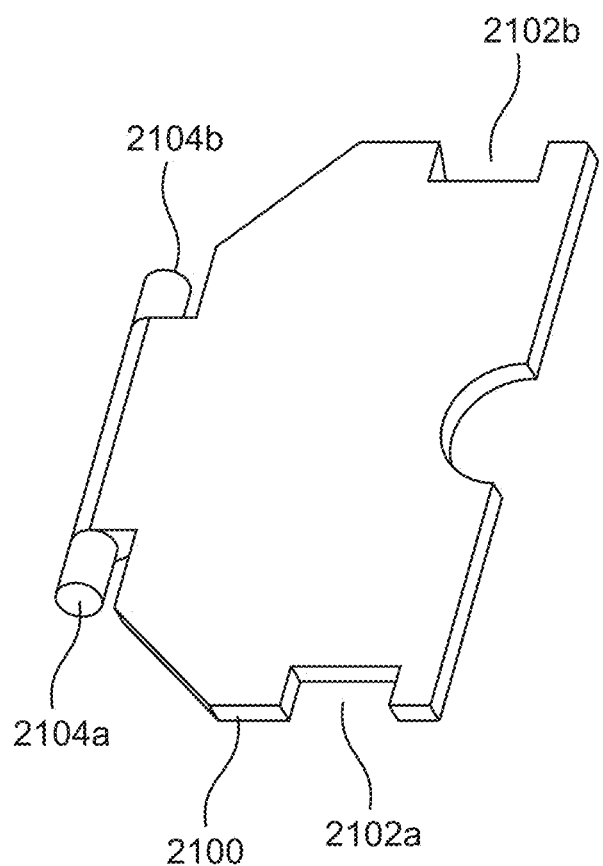
FIG. 21A
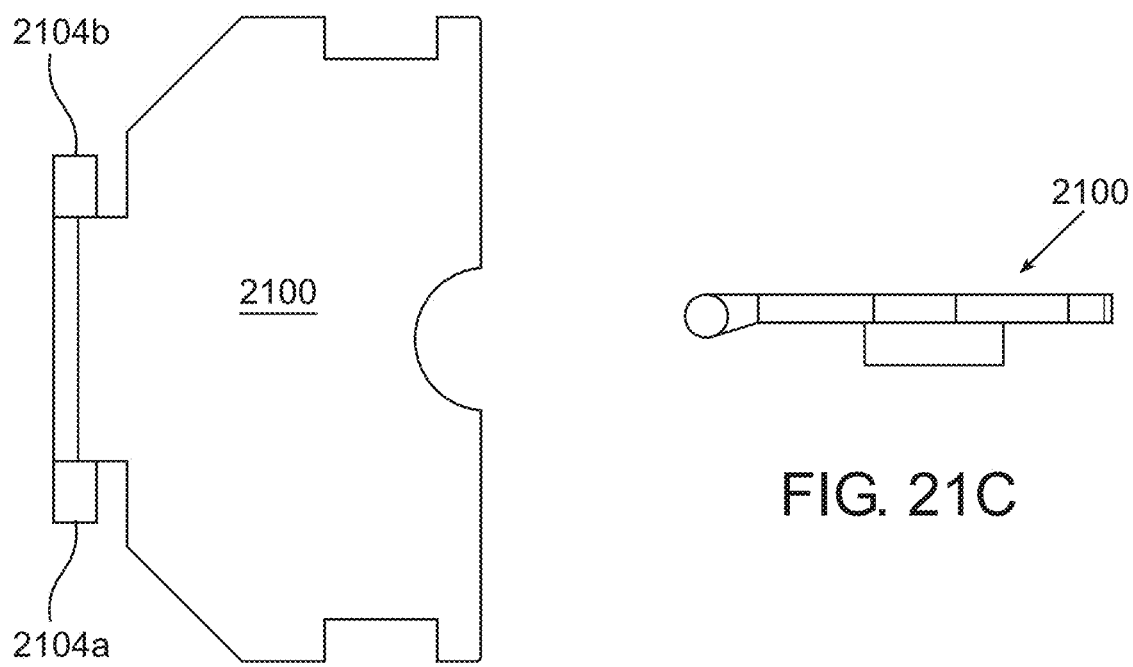
FIG. 21B
FIG. 21C

CATHETER ANCHOR SYSTEM AND METHOD THEREOF

CROSS-REFERENCE TO RELATED APPLICATION

This application is a continuation-in-part of U.S. application Ser. No. 16/027,300, filed on Jul. 4, 2018, which claims the benefit of U.S. Provisional Application No. 62/543,428, filed Aug. 10, 2017. The content of both applications are incorporated herein by reference in their entirety.

FIELD OF THE INVENTION

The present invention is directed to a method and system of and for securing a lumen or catheter, after placement in a patient, to prevent unwanted removal or dislodgement of the lumen or catheter caused by patient movement and/or further medical interventions such as cardiopulmonary resuscitation and the like. The securing of lumen and catheters in current practice is accomplished by suturing or in some cases supplemented with basic materials on hand like tape and gauze, rather than dedicated devices; therefore, this is a growing field with few well-established methods.

BACKGROUND OF THE INVENTION

Medical lumens or catheters are generally used to infuse a patient trans-natural —orifice or intravenously with medicative fluids, and/or for removing from a patient, urine, blood, or other fluids. A longtime and common problem after placing a catheter is securing or anchoring the catheter at or near its entry/exit point to prevent unwanted and possibly life threating removal or dislodgment of the lumen or catheter. A very common technique used to attempt to mitigate such unwanted removal is to use so-called "medical tape" in almost unlimited configurations in an attempt to "tape the catheter" to the patient. Such is typically effective with narrow diameter lumens catheters such as used for intravenous infusion at a patient's hand or forearm.

However, many specialized catheters or lumens are placed subcutaneously, such as but not limited to feeding tubes (i.e. jejunum or gastrostomy catheters or tubes and intrapleural catheters used to remove fluids or air from the thoracic cavity)(TABLE 1). It is difficult to tape these types of catheters or lumens to patients. Additionally, it is detrimental to the catheter or lumen's function if a "kink" or bend is inadvertently introduced during taping.

So-called "chest tubes" are typically placed via a thoracotomy; an incision between and/or through the ribs into the thoracic cavity. Once a catheter, lumen, or tube is inserted through a thoracotomy; typically, the tube is secured to the patient's skin with a surgical clamp, sutures, or adhesive patches or tape. However, these are limited methods of adhesion especially if further medical interventions are applied such as surgical procedures, cardiopulmonary chest compressions, electrical defibrillation, and the like.

A further variable related to medical catheters and lumens is the degree of arc or curve of the catheter as it enters/exits a patient. Related to intrapleural catheters or tubes, such are typically large in diameter and may be easily occluded or kinked if immediately bent and secured to a patient's chest. For a lack of an effective and efficient anchoring or securing means; many medical professionals utilize rolls of medical gauze around or beside the catheter and then secure with medical tape. However, such "ad hoc" methods are extremely ineffective for their intended purpose and use.

Known methods and systems used to various degrees of success in securing or anchoring an inserted catheter include: U.S. Pat. Nos. 4,838,878, 5,163,914, 5,292,312, 5,800,402, 6,132,399, 6,132,399, 6,387,076, 6,569,121, 7,749,199, 8,251,957, 9,248,259, 9,486,613, US20080200880, US20120245529, US20140207072, US20150119808, US20150367102, US20160114135.

It has been taught in medical practice that tape and gauze are the best means available at the moment. However, the "tape and gauze" method inevitably fails every time. The tape and gauze method does not attach firmly to the patient's chest for any length of time. The tape and gauze are bulky to the point of aiding in dislodgment and getting in the way of other definitive treatments such as CPR, defibrillation and EKG placement. Moreover, the tape and gauze method creates a bulky mass that is easily snagged or grabbed inadvertently in the heat of the moment. Lastly, the tape and gauze method requires more than one person and takes up precious moments of transport time.

It is desired to provide a catheter anchor method and system that efficiently secures medical devices to a patient. It is further desired to provide a method and system to overcome the above-mentioned and other disadvantages in the prior art.

SUMMARY OF THE INVENTION

It is an object of the present invention to provide a method and system of and for providing an anchor method and system for a medical device, such as a catheter.

It is an object of the present invention to provide a method and system of and for providing an anchor that is readily attached to patients and rapidly secured to different types of catheters or lumen.

It is an object of the present invention to provide a method and system of and for securing a catheter or lumen to a patient without bending or occluding flow through the catheter or lumen.

It is an object of the present invention to provide a method and system to secure a catheter to patient after a chest decompression has been performed.

It is an object of the present invention to provide a method and system to save time in securing a catheter to a patient while allowing full utilization of the catheter or lumen without interference with other treatments.

It is an object of the present invention to provide a method and system to secure chest needle decompression catheters, which are the prehospital/field/emergency treatment for tension pneumothoracies.

It is an object of the present invention to provide a method and system to secure a medical device, such as a Turkel system, at various lengths to a patient.

Objects of the invention are achieved by providing an apparatus for securing a medical device to a patient during a medical procedure, the apparatus comprising: a base having a top portion and a bottom portion, the base configured to be affixed to a patient via the bottom portion; at least one grommet secured within an aperture in the base; and at least one filler grommet configured to be secured within the aperture in the base, wherein the at least one filler grommet and at least one grommet are configured to attach the medical device to the base to hold the medical device in place during the medical procedure.

In certain embodiments, the apparatus further comprises a gasket, the gasket configured to be secured within the aperture in the base.

In certain embodiments, the bottom portion of the base is secured to the patient via adhesive, micro-suction, glue and combinations thereof.

In certain embodiments, the bottom portion of the base is secured to the patient via an adhesive pad, the adhesive pad occupying approximately ⅔ of a surface area of the bottom portion of the base.

In certain embodiments, approximately ⅓ of the bottom portion of the base includes micro-suction adhesive material with a seating hole for the medical device.

In certain embodiments, the medical device is selected from a group consisting of a needle decompression catheter for chest decompression, a central venous catheter, Turkel catheter, Tenckhoff catheter, Hemodialysis catheter, Hickman line, Groshong line, Quinton catheter, Huber needle, percutaneous endoscopic gastronomy feeding tube, peripherally inserted central catheter, intrauterine pressure catheter, pulmonary artery catheter, Swan-Ganz catheter, and suprapubic catheter.

In certain embodiments, the apparatus is pre-attached to the intended medical device being inserted into the patient. This allows for an even more streamlined application of the invention and requires integration with an existing medical device from the group listed above.

In certain embodiments, the at least one filler grommet has an outer diameter slightly smaller than a slightly larger inner diameter of the grommet.

In certain embodiments, there is a physical connection between the grommet and the filler grommet.

In certain embodiments, the apparatus further comprises at least one clip ring and at least one adhesive strip attached to the base adjacent to the grommet and extending away from the grommet, the at least one clip able to support varying lengths of the medical apparatus.

In certain embodiments, the at least one clip ring is slidable on the adhesive strip.

In certain embodiments, the base is a rigid body or a flexible base.

In certain embodiments, the at least one grommet and the at least one filler grommet are shaped as ellipses, squares, triangles, hexagons, circles, and combinations thereof.

In certain embodiments, the filler grommet is attached to the base via a wire or cord.

In certain embodiments, the grommet, rings, or gaskets are made from rubber, plastic, silicone, and combinations thereof.

In certain embodiments, the apparatus is three dimensionally printed and thereby customized to conform to the patient.

In certain embodiments, the apparatus is made via additive manufacturing techniques.

Other objects of the invention are achieved by providing a method for securing a medical device to a patient during a medical procedure, the method comprising the following steps: providing an apparatus; securing the base to a skin surface of a patient; inserting the medical device into the patient through the aperture in the base; inserting the grommet into the base; and inserting the filler grommet within the aperture in the base, wherein the at least one filler grommet and at least one grommet attach the medical device to the base.

In certain embodiments, the method includes inserting a gasket into the aperture in the base to secure the at least one grommet to the filler grommet.

In certain embodiments, the bottom portion of the base is secured to the patient via adhesive, micro-suction, glue and combinations thereof.

In certain embodiments, the method includes providing at least one clip ring and at least one adhesive strip attached to the base adjacent to the grommet and extending away from the grommet, the at least one clip able to support varying lengths of the medical apparatus.

In certain embodiments, the method includes sliding the at least one clip ring on the adhesive strip to support the varying lengths of the medical apparatus.

Other objects of the invention are achieved by providing silicon rubber on plastic friction mechanisms to secure the catheter.

In certain embodiments, an aperture base is designed to allow catheters of many sizes, small to large, while the dimension range is not too large so as to allow excessive movement.

It in certain embodiments, it is contemplated that additional features for securing the tubing can be supplemented onto the device to accommodate outlier medical devices or medical devices having unique configurations.

Other objects of the invention are achieved by providing an apparatus for securing a medical device to a patient designed with superior adhesion technology to sustain high traffic and disturbance areas. The oil effusing, soft and malleable skin surface of a patient presents a difficult area to secure, especially during strong perturbations, such as those experienced during chest decompressions. Recent advances in micro-suction and other medical adhesive technologies such as double coating allow the base to reliably attach to any patient on almost any point of their anatomy Other objects of the invention are achieved by providing an apparatus that would require only a single person as opposed to the multiple personnel needed for current attempts to secure needle decompression catheters.

Other objects of the invention are achieved by providing an apparatus that would allow for specific depth placement and retention at said depth of medical devices. This would obviate the need for the "burying/tunneling" of the Turkel catheter, which reduces the risk of harming internal tissues or organs. This versatile innovation also precludes the need for excessive sutures and surgical methods for securing the catheter that would add unnecessary risk to the patient.

Objects of the invention are achieved by providing systems, devices and methods which include a coating selected from the group consisting of an anti-microbial, an anti-bacterial, an anti-hemorrhagic agent, and combinations thereof.

According to a first aspect of the embodiments, an apparatus for securing a medical device to a patient during a medical procedure is provided, the apparatus comprising: a base having a top portion, a bottom portion, and an aperture located on the bottom portion, and wherein the base is configured to be affixed to a patient via the bottom portion; and a medical device securing assembly configured to be secured within the aperture in the base, the medical device securing assembly comprising a substantially cubic enclosure, a pair of closable doors, and a retention pad, the retention pad secured to an underside of each of the pair of closable doors, and wherein the medical device securing assembly is further configured to attach the medical device to the base to hold the medical device in place during the medical procedure.

According to the first aspect of the embodiments, the bottom portion of the base is secured to the patient via adhesive, micro-suction, glue and combinations thereof.

According to the first aspect of the embodiments, the bottom portion of the base is secured to the patient via an adhesive pad, the adhesive pad occupying approximately ⅔ of a surface area of the bottom portion of the base.

According to the first aspect of the embodiments, approximately ⅓ of the bottom portion of the base includes micro-suction adhesive material with a seating hole for the medical device.

According to the first aspect of the embodiments, the medical device is selected from a group consisting of a needle decompression catheter for chest decompression, a central venous catheter, Turkel catheter, Tenckhoff catheter, Hemodialysis catheter, Hickman line, Groshong line, Quinton catheter, Huber needle, percutaneous endoscopic gastronomy feeding tube, peripherally inserted central catheter, intrauterine pressure catheter, pulmonary artery catheter, Swan-Ganz catheter, and suprapubic catheter.

According to the first aspect of the embodiments, the medical device intended for insertion into the patient is pre-attached to the apparatus According to the first aspect of the embodiments, the apparatus further comprises at least one clip ring and at least one adhesive strip attached to the base adjacent to the medical device securing assembly and extending away from the medical device securing assembly, the at least one clip able to support varying lengths of the medical apparatus.

According to the first aspect of the embodiments, the at least one clip ring is slidable on the adhesive strip.

According to the first aspect of the embodiments, the base is a rigid body or a flexible base.

According to the first aspect of the embodiments, the medical device securing assembly further comprises: a plurality of nubs protruding from an inner surface of a base of the medical device securing assembly, each of the plurality of nubs imparting a force on the retention pad when the pair of closable doors are closed, causing the retention pad to frictional engage the medical device.

According to the first aspect of the embodiments, the medical device securing assembly further comprises: a pair of locking tabs located on each of the pair of closable doors; and a pair of locking tab receptacles for each of a respective pair of locking tabs, the locking tab receptacles located on sides of the enclosure, each of the locking tab receptacles configured to accept a respective locking tab such that the closable doors are substantially locked in place.

According to the first aspect of the embodiments, the medical device securing assembly further comprises: a retention pad retaining ridge located on an inner surface of each of the pair of closable doors, the retention pad retaining ridge configured to hold the retention pad substantially in place.

According to the first aspect of the embodiments, the retention pad is held in place on the inner surface of the closable door by one of glue and ultra-sonic welding.

According to the first aspect of the embodiments, the medical device securing assembly further comprises: an aperture located through the base of the enclosure such that the medical device can substantially ready pass through the medical device securing assembly.

According to the first aspect of the embodiments, the medical device securing assembly further comprises: a pair of hinge receptacles located on two opposing walls of the enclosure; and a pair of hinge protrusions located on opposing sides of a detachable locking door, wherein the hinge protrusions are configured to fit within respective hinge receptacles.

According to the first aspect of the embodiments, the enclosure and retention pad are made from rubber, plastic, silicone, and combinations thereof.

According to the first aspect of the embodiments, the apparatus is three dimensionally printed and thereby customized to conform to the patient.

According to a second aspect of the embodiments, a method is provided for securing a medical device to a patient during a medical procedure, the method comprising the following steps: providing an apparatus comprising: a base having a top portion, a bottom portion, and an aperture located on the bottom portion, and wherein the base is configured to be affixed to a patient via the bottom portion; and a medical device securing assembly configured to be secured within the aperture in the base, the medical device securing assembly comprising a substantially cubic enclosure, a pair of closable doors, and a retention pad, the retention pad secured to an underside of each of the pair of closable doors, and wherein the medical device securing assembly is further configured to attach the medical device to the base to hold the medical device in place during the medical procedure; securing the base to a skin surface of a patient; inserting the medical device into the patient through the aperture in the base and the medical device securing assembly; and closing the lockable doors such that the medical device is attached to the base.

According to the second aspect of the embodiments, the bottom portion of the base is secured to the patient via adhesive, micro-suction, glue and combinations thereof.

Objects of the invention and its particular features and advantages will become more apparent from consideration of the following drawings and accompanying detailed description. Variations from the description above may and can be made by one skilled in the art without departing from the scope of the invention. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIGS. 17A-17E illustrates several views of a second embodiment of a catheter securing assembly or components thereof according to further aspects of the embodiments.

FIGS. 18A-18E illustrates several views of a third embodiment of a catheter securing assembly or components thereof according to further aspects of the embodiments.

FIGS. 20A-20E illustrates several views of a fifth embodiment of a catheter securing assembly or components thereof according to further aspects of the embodiments.

FIGS. 21A-21C illustrate several views of a locking door for use with the fifth embodiment of the catheter securing assembly shown in FIGS. 20A-20E according to further aspects of the embodiments.

DETAILED DESCRIPTION OF THE INVENTION

In the following description, numerous details are set forth for the purpose of example and explanation; however, one of ordinary skill in the art will realize that the invention may be practiced without the use of these specific details. The device as shown involves a catheter securing that utilizes a plastic-on-rubber friction dependent bond. However, other medical devices may be used with the apparatus and system of the present invention.

The Appendix to the application is incorporated by reference herein in its entirety.

Figure 1:
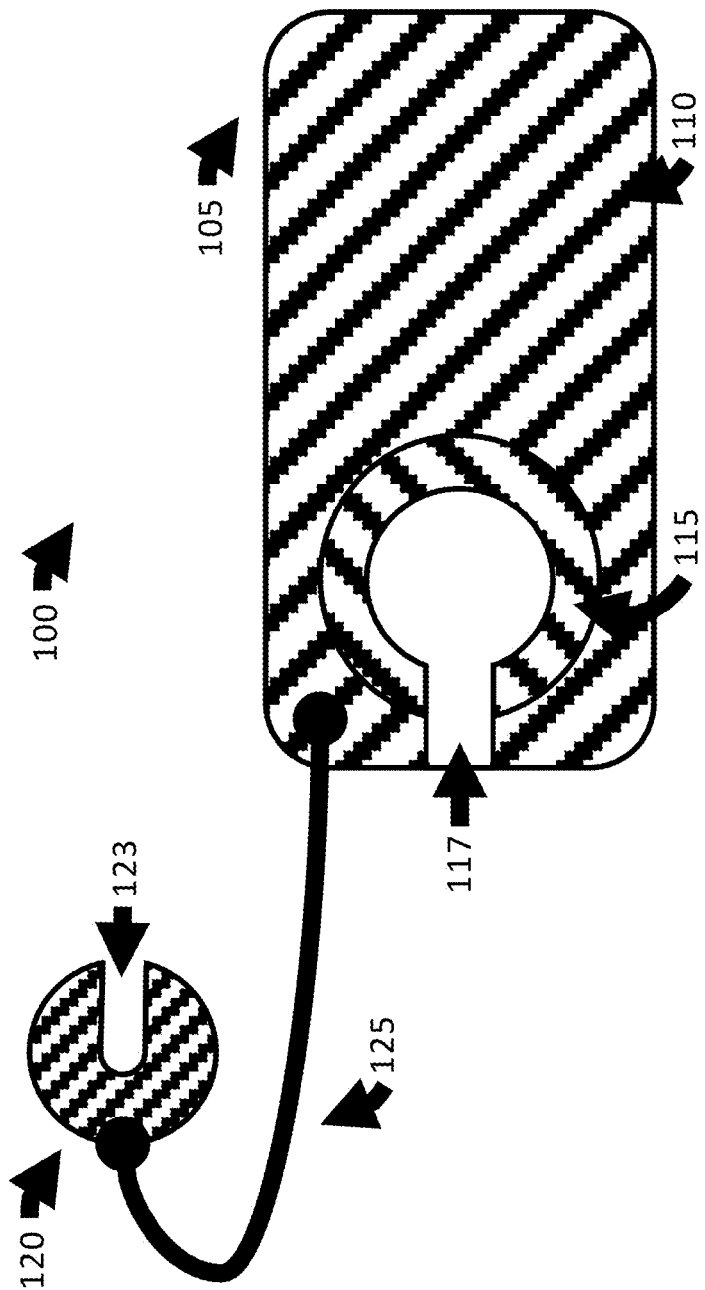
FIG. 1 is a top schematic diagram depicting an embodiment of the inventive method and system.
Figure 2:
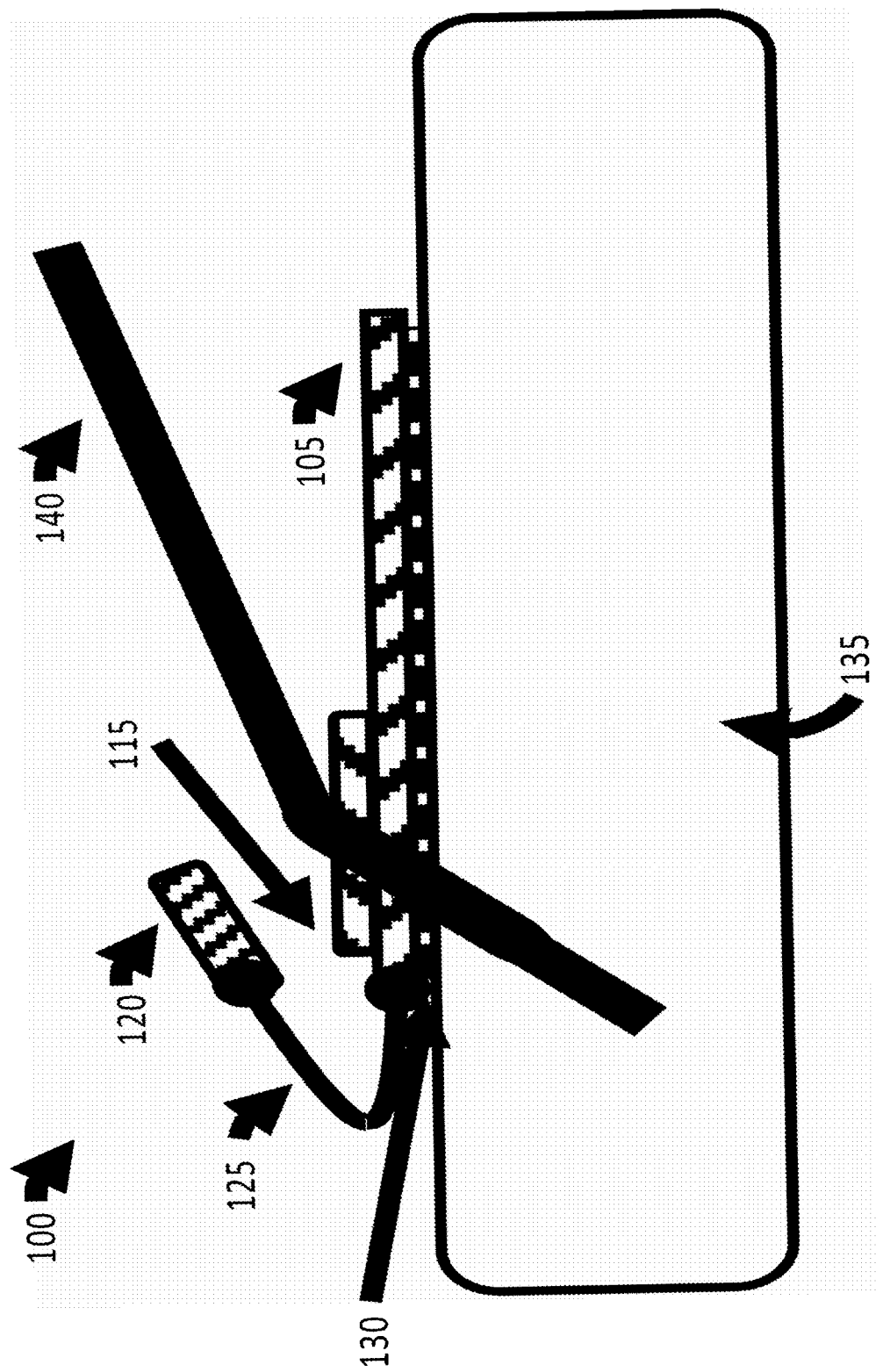
FIG. 2 is a side-view schematic diagram depicting an embodiment of the inventive method and system.
Figure 3A:
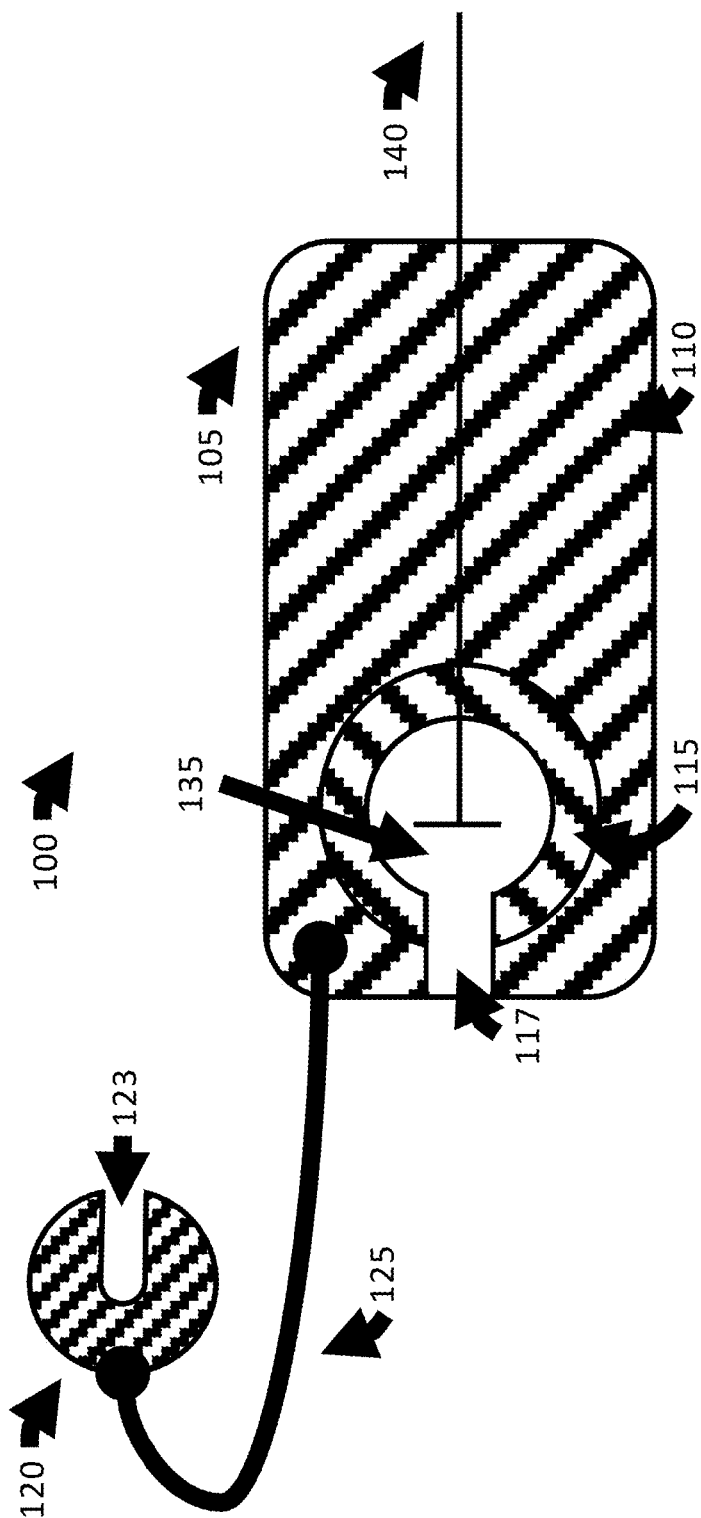
FIGS. 3A & 3B are schematic diagrams depicting embodiments of the inventive method and system while securing a catheter.
Figure 3B:
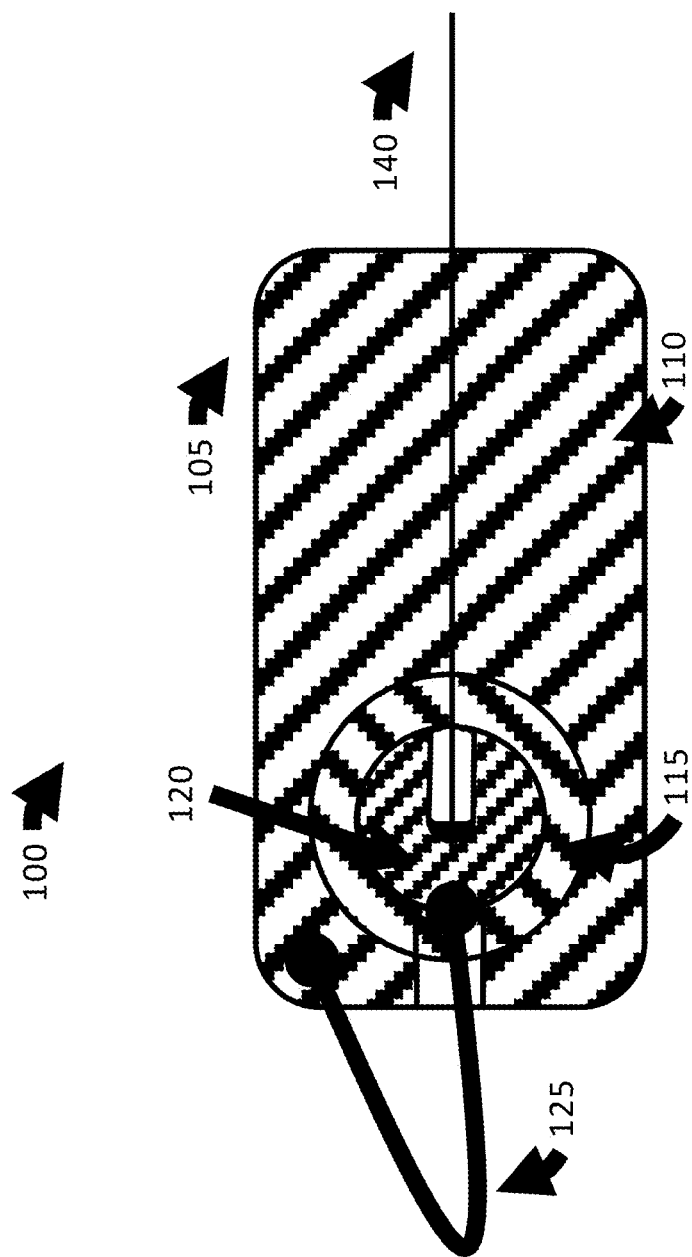
Figure 4:
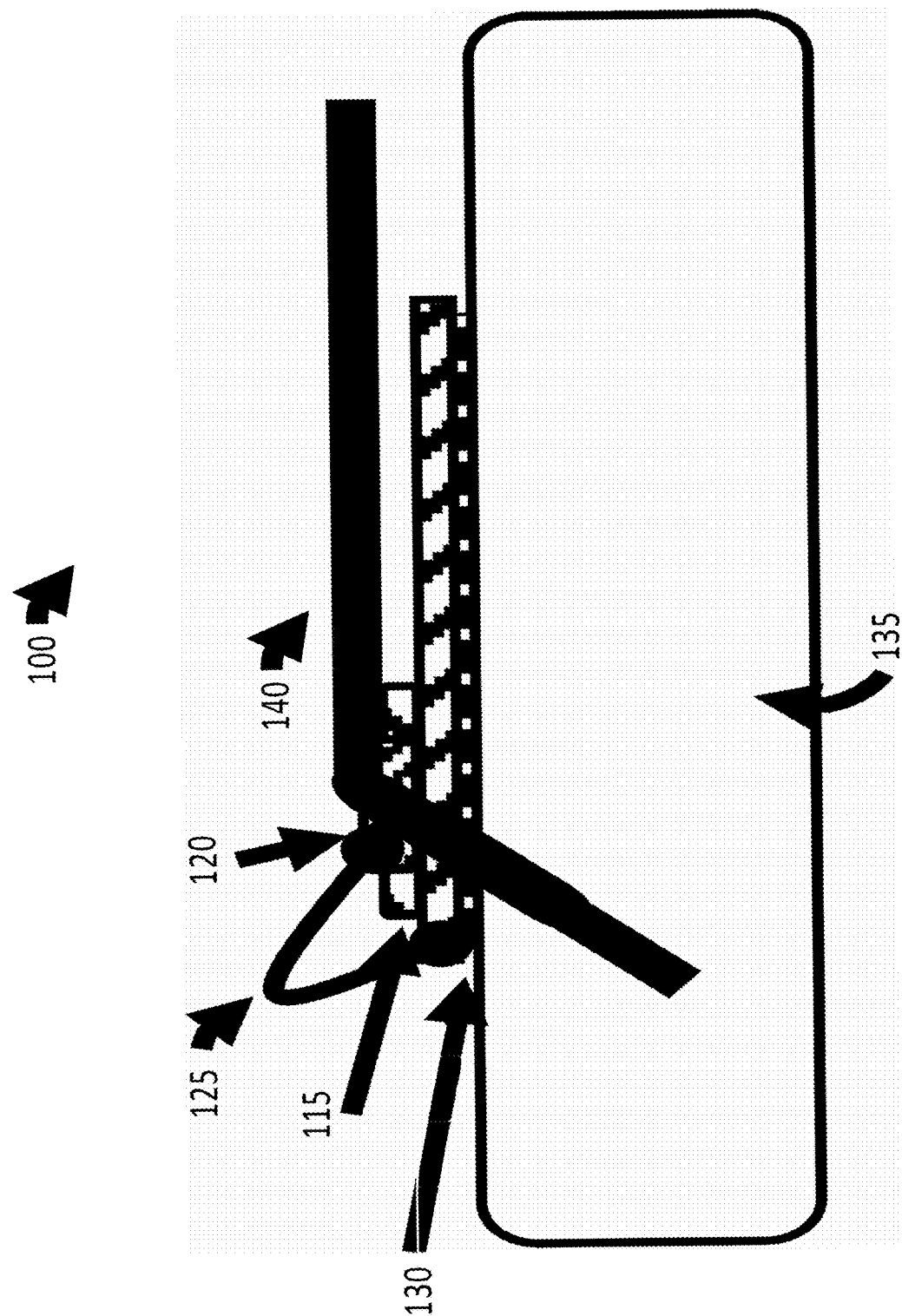
FIG. 4 is a side-view schematic diagram depicting embodiments of the inventive method and system while securing a catheter.

As depicted in FIG. 1 and FIG. 2, an embodiment of the inventive method and system (100) includes a flexible or semi flexible base or pad (105) having a top portion (110) a first grommet (115) affixed to the base (105) and a second "filler" grommet (120) optionally connected to the base (105) with and by a tether (125). It is contemplated that the first and second grommets (115, 120) include cut-out portions (117 and 123 respectively) to provide access of the optional tether (125) and/or a catheter or lumen (140).

It is contemplated that the base (105) includes a medical adhesive (130) to removably affix the base (105) to a patient (135). Depending upon the medical circumstances, the base (105) may be affixed to a patient (135) before or after a catheter or lumen (140) is placed in a patient (135). In certain embodiments, portions of the base (105) may include a medical adhesive (130), such as ⅓ of the base or ⅔ of the base. In various embodiments, different mechanisms are used to secure the base to the patient.

As depicted in FIGS. 3A, 3B, 4, and 5, after a catheter or lumen (140) is placed within a patient (135) and the base (105) affixed to the patient (135), the second grommet is removably secured within the first grommet (115) via a press or friction fit and/or medical adhesive (not shown). It is contemplated that the dimensional configuration of the second grommet (120) provides frictional tension between the catheter or lumen (140) and the first grommet (115), thus mitigating or preventing the catheter or lumen (140) from being inadvertently removed or dislodged from a patient (135) while preventing an excessive degree of arc or bend to the catheter or lumen (140). It is contemplated that medical adhesive (not shown) may also be used to removably secure or affix the second grommet (120) to the first grommet (115) and/or the catheter or lumen (140).

Figure 5:
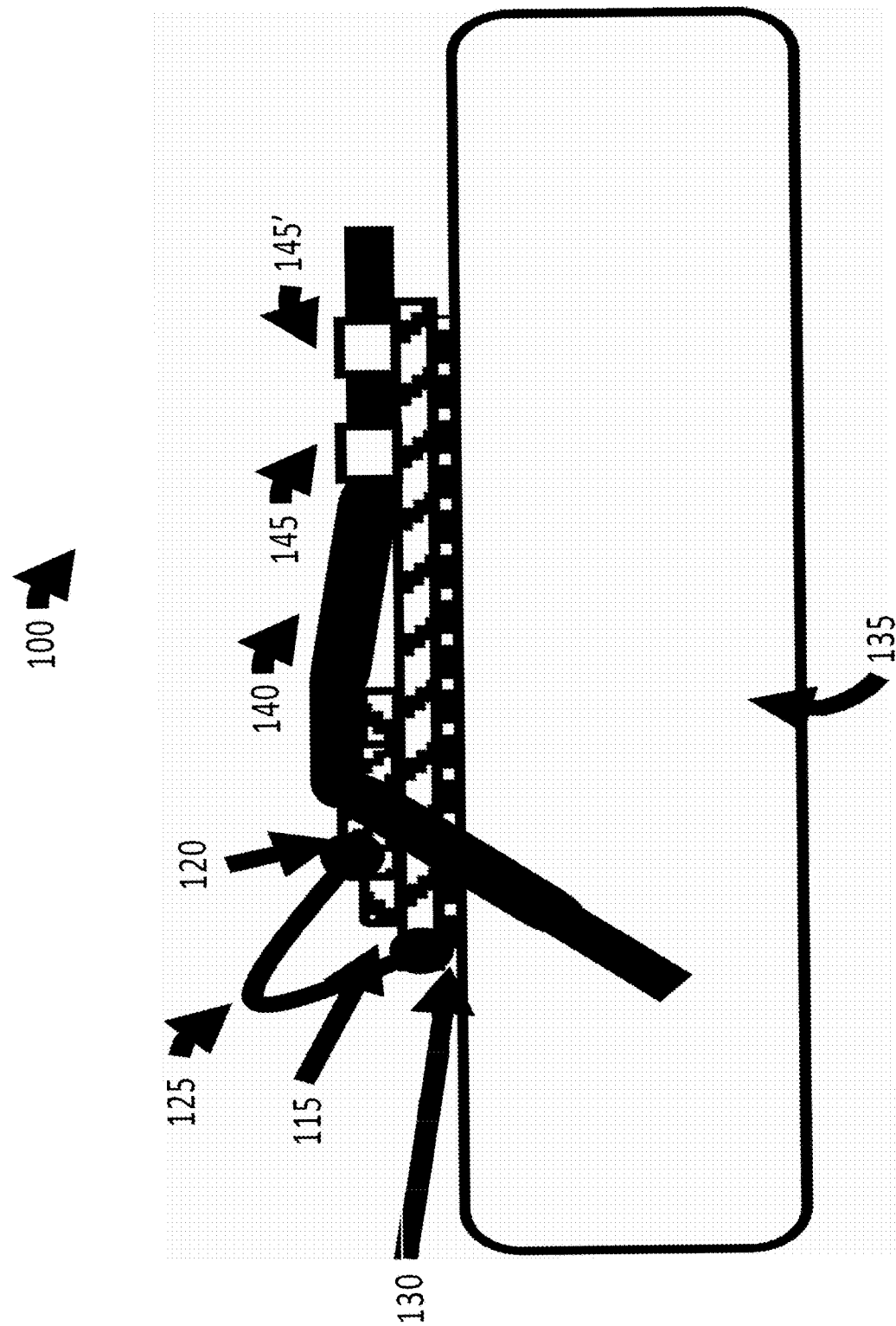
FIG. 5 is a side-view schematic diagram depicting embodiments of the inventive method and system while securing a catheter with additional straps.
Figure 6:
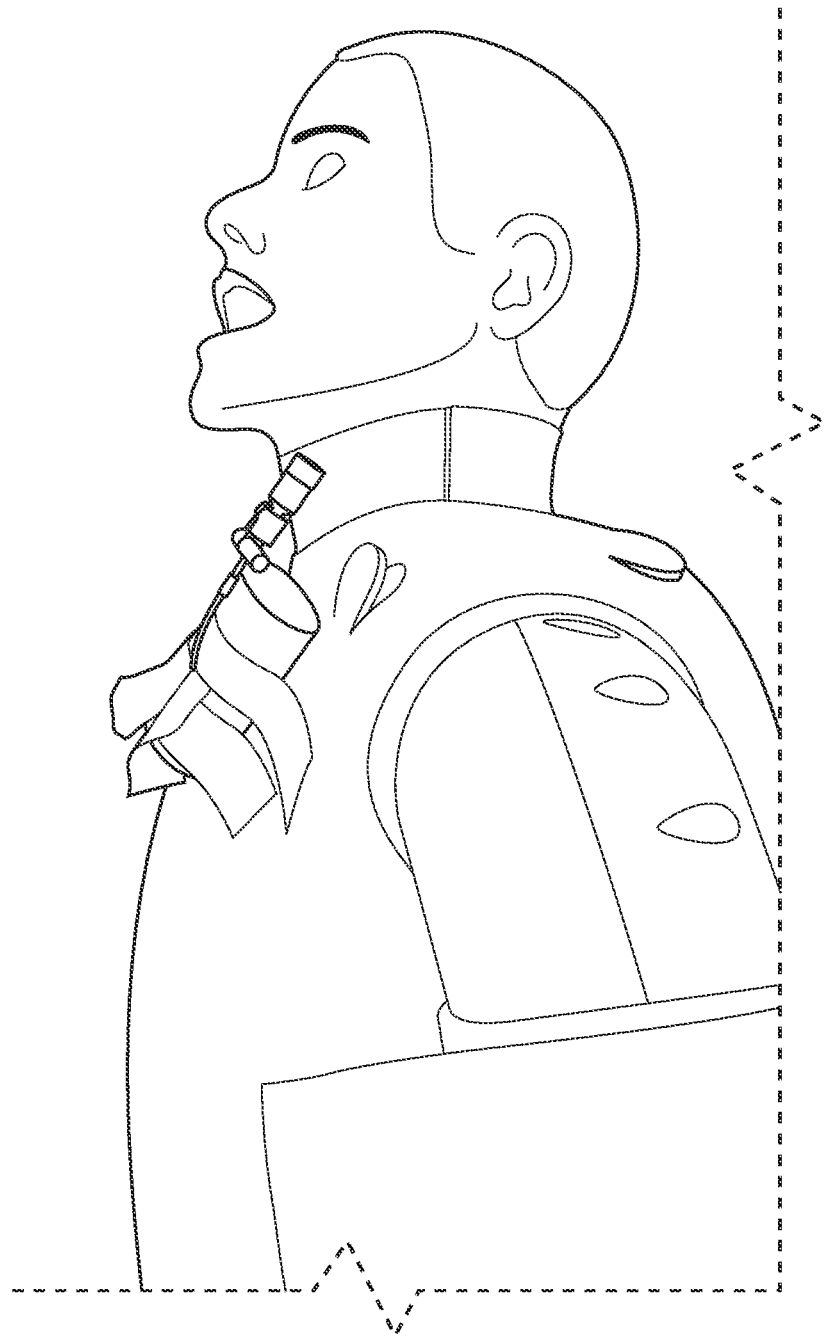
FIGS. 6-11 are photographs of an embodiment of the inventive method and system.
Figure 7:
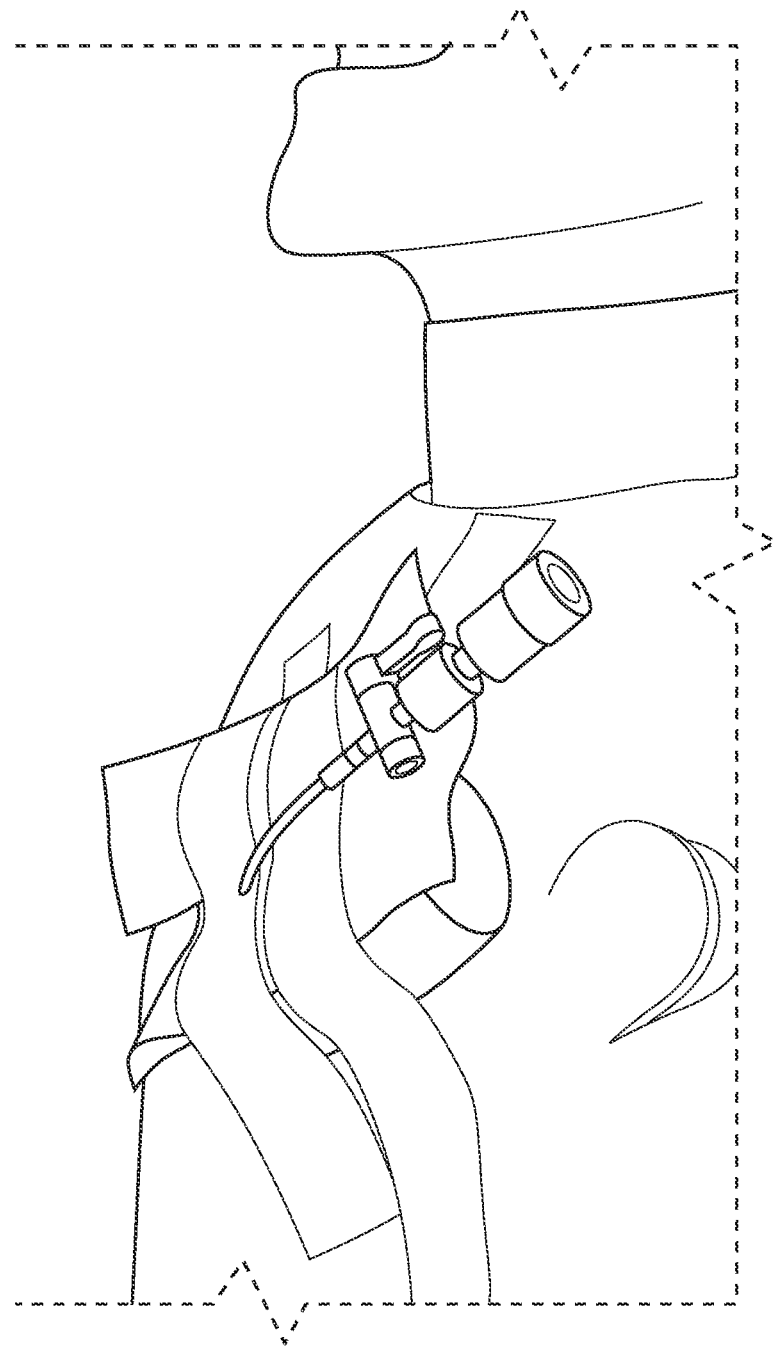

As depicted in FIG. 5, the base (105) may include clips, grommets, or hollow gaskets (145, 145') to further secure the catheter or lumen (140) to the base (105) also providing "strain relief" to the first and second grommets (115, 120).

It is contemplated that the system is intended to secure the catheter (140) after a chest decompression has been performed. To this end, the base (110) of the system has been designed to securely attach to the patients' chest and sustain substantial external forces that are diffused over the wide surface area and multiple points of contact. The adhesive material (130) assists in this regard and can be selected to optimize either the stability or flexibility of placement.

It is contemplated that the device saves time vs the old method of securement. To this end, simple components that are easy to manipulate by a single personnel were included. The plastic and silicon grommets are rapidly connected, thereby securing the catheter and completing the method in a fraction of the time typically used to tape and gauze the exposed tubing. Additionally, the device can be pre-attached to the medical device intended for securement before it is event inserted, thereby saving even more time during the procedure.

It is contemplated that the device secures the catheter in a manner that still allows full utilization but allows it to no longer interfere with other treatments. Apertures in the rubber grommets are able to guide the external portion of the tubing, allowing full functional use, and preventing bends or kinks that would otherwise risk occluding the flow of materials through the tube. Additionally, the base can be flexible or rigid depending on which accommodates the anatomy of the catheter site better. It is contemplated that certain embodiments of the invention will include a three dimensionally printed base that is tailored to the patient's anatomy, thereby achieving a more perfect fit and maintaining full utilization of the catheter.

It is contemplated that the invention uses silicon rubber on plastic friction mechanism to secure a catheter to a patient.

In certain embodiments, the device includes superior adhesion for high traffic/disturbance area.

In certain embodiments, the gasket is specially designed to stop kinking of Turkel as it bends and helps prevent hubs of (top of) 14 gauge needle decompression catheters from folding over and being useless/ineffective for treatment.

In certain embodiments, the device has various shapes and configurations but operates via a principle of operation of attaching a medical device, such as a catheter, to a patient without the need for tape or gauze.

In certain embodiments, the device has a grommet and filler grommet having a circular or disc like shape and having an aperture at one end of the circular or disc like shape. In such an embodiment, a catheter can be slide into the aperture in the grommet and filler grommet, and the catheter can be held in place by frictional forces.

In certain embodiments, the catheter is force fit within the aperture in the grommet and filler grommet.

In certain embodiments, the device is made or rubber, silicon or other materials.

In certain embodiments, the adhesive to secure the device to a patient is a hydrogel adhesive.

In certain embodiments, the bottom portion of the device has a liner that can be pulled to expose the adhesive and stick the device onto a patient.

In certain embodiments, a strap is attached at one end to the base along with an accompanying loop that is attached longitudinally on the base, wherein the strap is tapered so that the unattached end is slightly wider than the loop opening. This allows the user to easily secure the exposed end of the medical tubing securely to the base by pulling the strap through the accompanying loop, thus securing the strap in place.

In certain embodiments, a holding member is secured via an adhesive to the base wherein a strap is secured at one end to a holding member. In certain embodiments, the strap is secured at one end under the holding member.

Components of Embodiment of System

In certain embodiments, system has various parts as shown in FIGS. 6-11.

Figure 8:
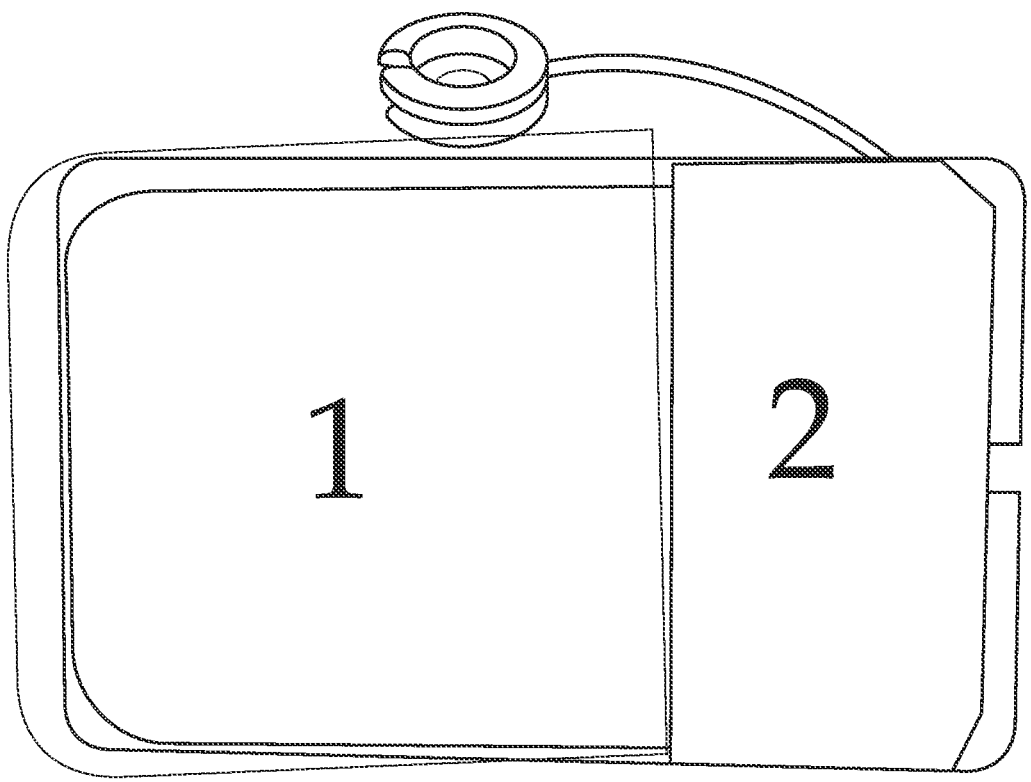
Figure 9:
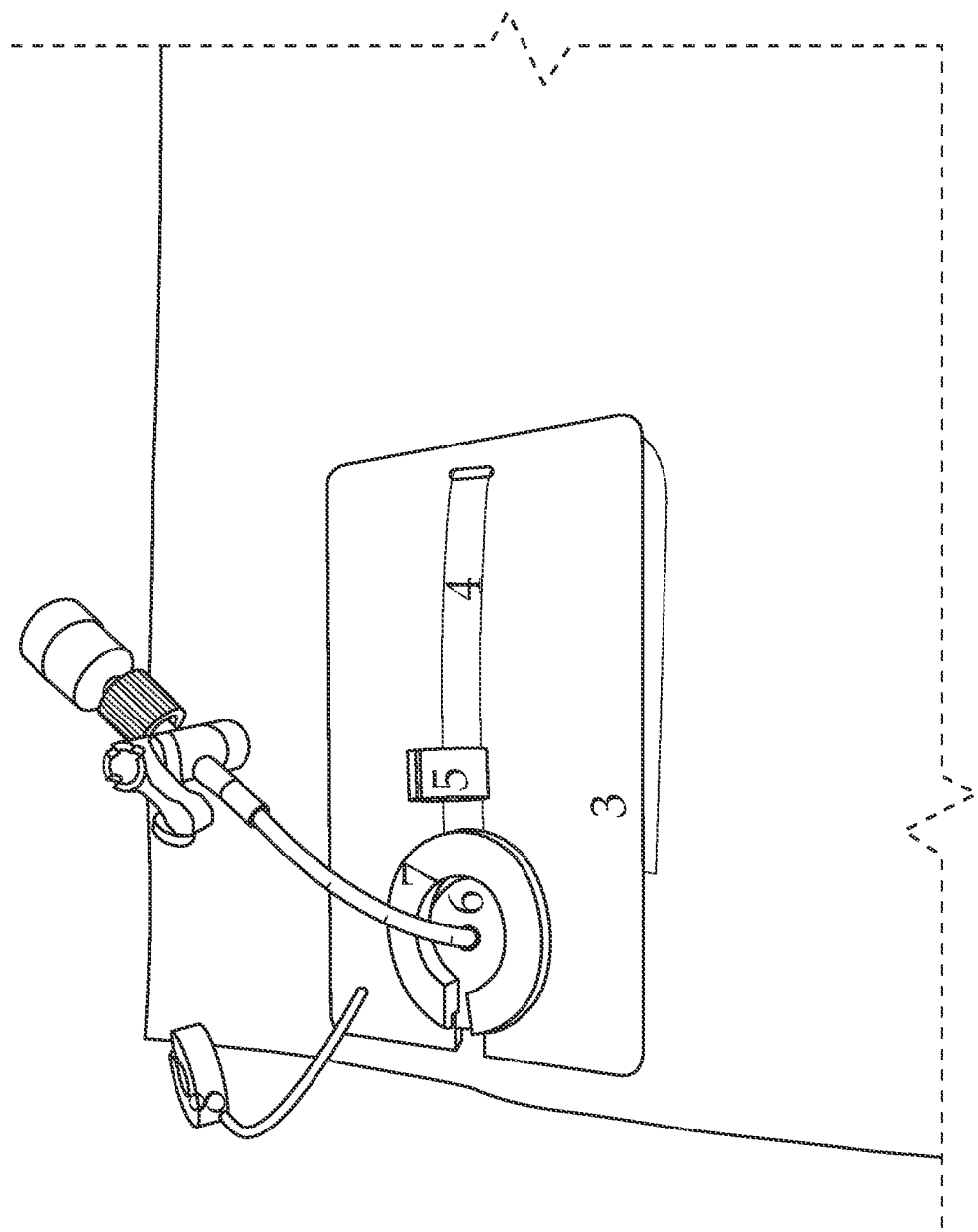
Figure 10:
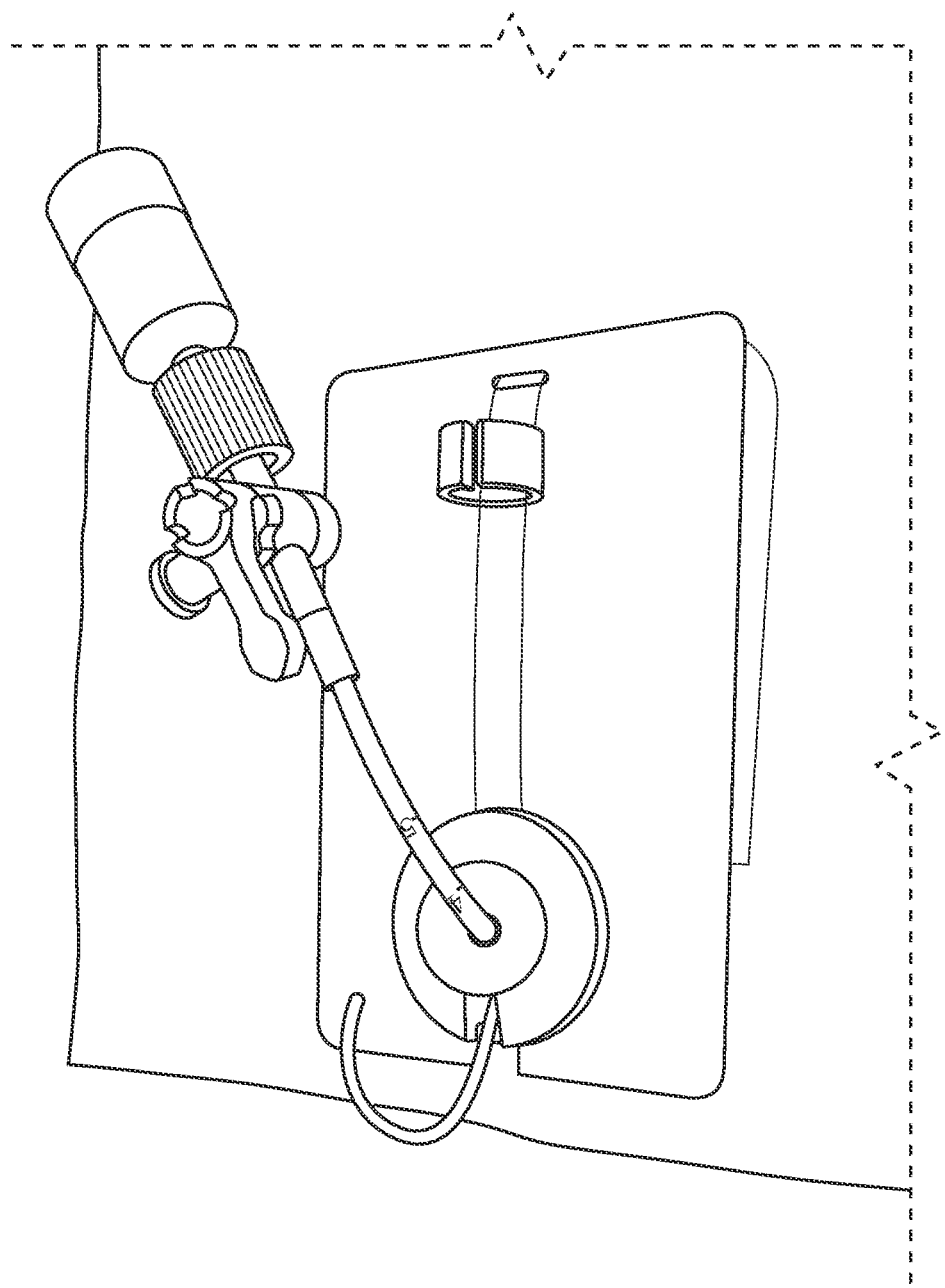
Figure 11:
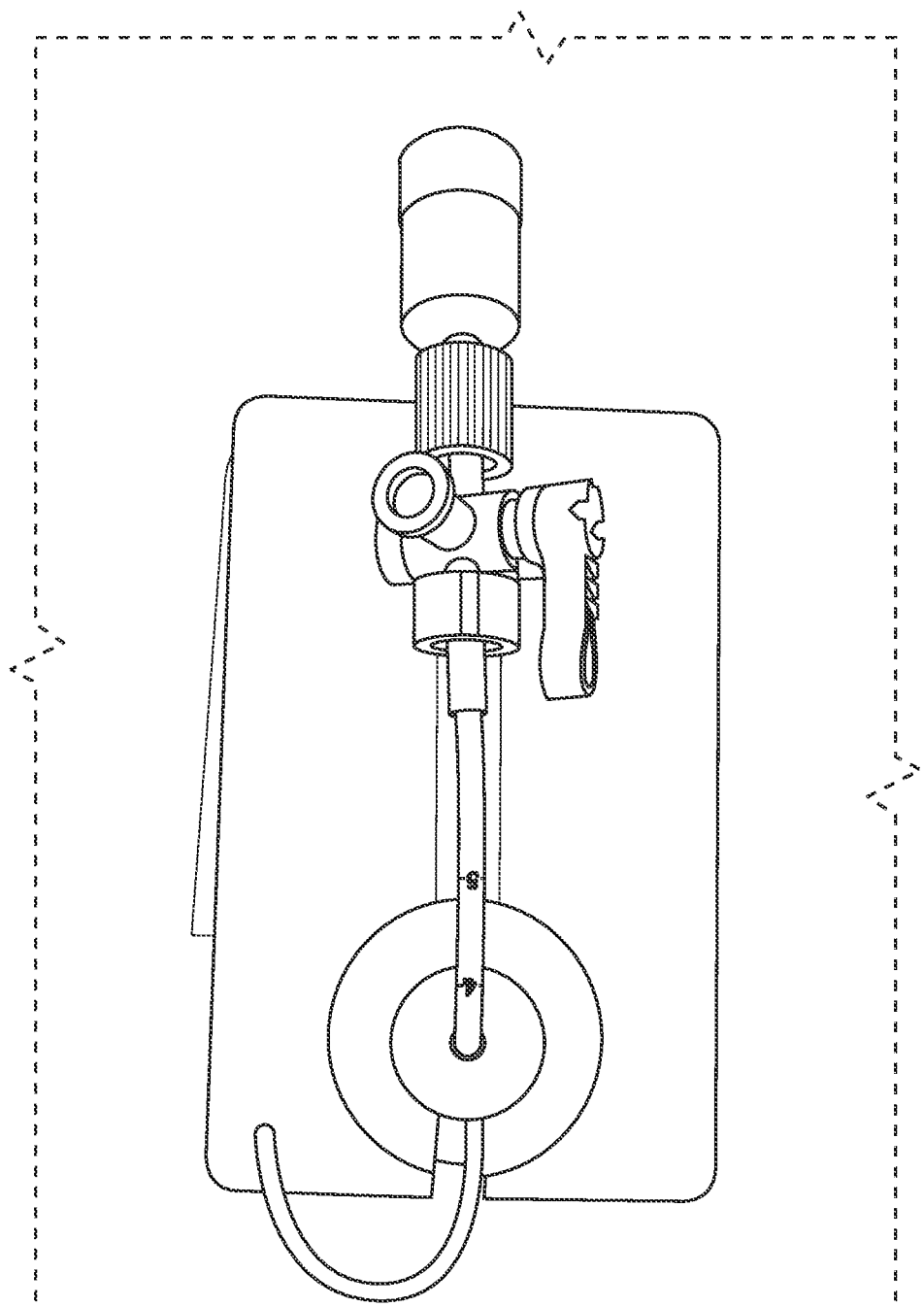

In FIGS. 8-9, the parts are numbered namely:
Part 1—adhesive pad with tensile strength similar to that of a defibrillation pad. Occupies approximately ⅔ of underside of device. Part 1 is used for anchoring device to patient.
Part 2—Micro-suction adhesive material with a cut to allow for easy placement and a seating hole for catheter. Part 2 still retains adhesiveness after several uses is wiped off with alcohol prep or water. Part 2 adheres to catheter and filler grommet.
Part 3—Standard size (CR80) plastic PVC card/pad with 20-30 mil thickness with a funnel slot cut into one end to feed catheter to center of ⅝ hole also cut into the plastic. This card has two more small cuts. One unseen under part 7 and one slightly from the top. Part 4 is fed through these last two mentioned slots.
Part 4—Plastic strip cut from 0.007 thickness clear plastic. Woven through two slits cut into plastic card/pad. Part 4 is the anchoring system for part 5.
Part 5—Plastic 8 mm diameter clip rings. These rings can be locked and unlocked with ease. This clip slides along length of plastic strip based on clinicians need as the amount of catheter exposed will vary from patient to patient.
Part 6—A ⅝ diameter hole cut to allow catheter to be fed into micro suction adhesive pad which lies beneath this hole. Also used for part 7 to surround the catheter.
Part 7—A rubber/plastic/silicone o ring or gasket type ring. Surrounds part 6 and holds part 8. Also serves as a cushion and protector for the catheter when it is laid down to be secured.
Part 8—Filler and holder grommet. Has a small triangle section removed to feed catheter through with a seating hole slightly smaller than then diameter of the catheter to create plastic on plastic "friction bond". After being placed around catheter it is snuggly fit into the O-ring gasket. The micro-suction adhesive adheres to aid in the retention created by the snug fit. This grommet attaches to card/pad via a length of silicone akin to a small headphone wire. This length of silicone is attached through a small hole in the base of the device.

Method of Operation

In certain embodiments, the method involves first removing the adhesive protector from micro-suction pad.

The second step involves feeding the base of exposed portion of catheter into seating hole in micro-suction pad via slot.

The third step involves removing the adhesive back of anchoring pad.

The fourth step involves applying the anchoring pad to patient.

The fifth step involves attaching the holder grommet to catheter with small triangle cut facing towards the 8 mm plastic clip and slide mechanism.

The sixth step involves firmly seating the catheter into O-ring.

The seventh step involves sliding 8 mm clip to appropriate point for remaining length of catheter.

The eighth step involves opening the and securing it shut around the catheter.

Additional Inventive Features and Components of System

In certain embodiments, instead of the filler grommet attached to the base of the card, a strip of adhesive material is used to wrap around the base of the catheter.

In certain embodiments, the device can be adjusted to fit varying lengths of a catheter and can be used to secure the catheter to a patient.

The anchoring system replaces an archaic and ineffective means for securing a unique type of catheter. Due to the uniqueness of the catheter, i.e. size, variable depth of placement, and heaviness, it requires a means of securing that is only made possible by the device described herein. The device addresses and resolves a long-standing problem by way of the above noted reasons.

The device also establishes a new principle of operation. It not only eliminates the bulk, but it also provides an adaptive means of securing the top-heavy portion of the catheter, whether there is unused length or the entirety of the catheter is inserted.

The device is configured to accommodate and secure the variance in utilized length specific to heavy catheters. This variance can be substantial depending on the function of the catheter and where it is placed on the patient.

In certain embodiments, alternate clear plastic strap having adhesive ends is provided that secures the remaining length of the catheter. In certain embodiments, this is an alternative to the 8 mm diameter clip rings.

In one or more embodiments the method further comprises sliding the at least one clip ring on the adhesive strip to support the varying lengths of the medical apparatus.

Attention is now directed towards FIGS. 12-26, which illustrate a second general embodiments of a catheter securing mechanism as describe herein in regard to FIGS. 1-11 and device 100. Since the second general embodiments is designed to operate under substantially similar circumstances and in a substantially similar environment (i.e., on a human patient or person under care), much of the discussion previously provided that covers such areas can be omitted in fulfillment of the dual purposes of clarity and brevity. Notwithstanding that FIGS. 12-26 illustrate a second major or general embodiment of the catheter securing mechanism or system of FIGS. 1-11, it is to be noted, and as discussed below, there are several modifications to this embodiment that are shown in FIGS. 12-26. That is, there is at least several additional and different embodiments/alternations/ modifications of the second general embodiment of the catheter securing mechanism shown in FIGS. 12-26.

Referring back to FIG. 1 and FIG. 2, aspect of the embodiments include a flexible or semi flexible base or pad (105) having a top portion (110) a first grommet (115) affixed to the base (105) and a second "filler" grommet (120) optionally connected to the base (105) with and by a tether (125). It is contemplated that the first and second grommets (115, 120) include cut-out portions (117 and 123 respectively) to provide access of the optional tether (125) and/or a catheter or lumen (140). According to the further aspects of the embodiments shown in FIGS. 12-26, first and second grommets 115, 120 are replaced by any one of catheter securing assemblies 1200, 1700, 1800, 1900, 2000, 2400, and 2600 (for the purposes of the following discussion reference shall be made only to catheter securing assembly 1200, unless and until other assemblies are specifically mentioned, as the aforementioned assemblies are substantially similar in terms of size, structure, and functionality).

Figure 12:
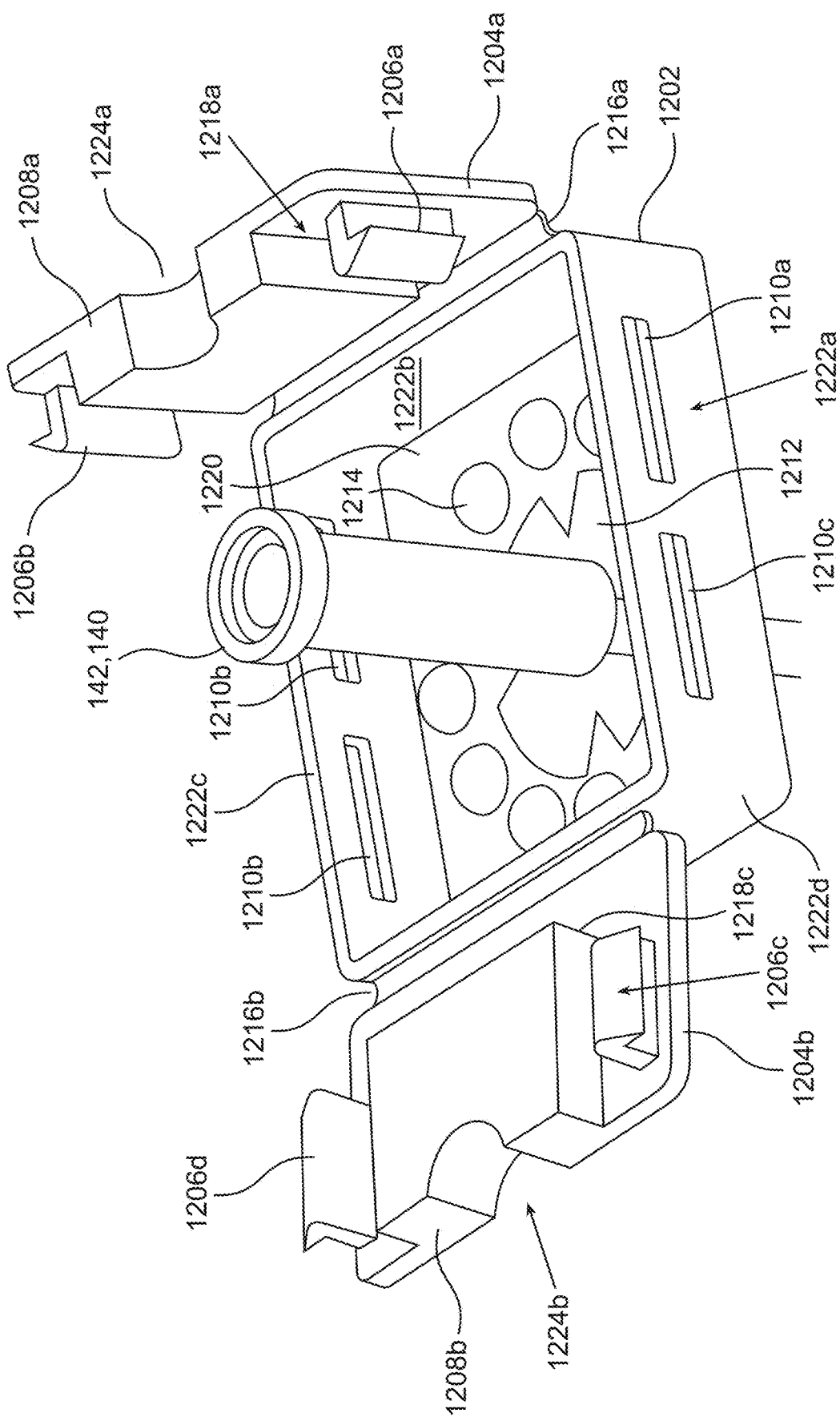
FIG. 12 illustrates a top perspective view of a catheter securing assembly when opened according to further aspects of the embodiments.
Figure 13:
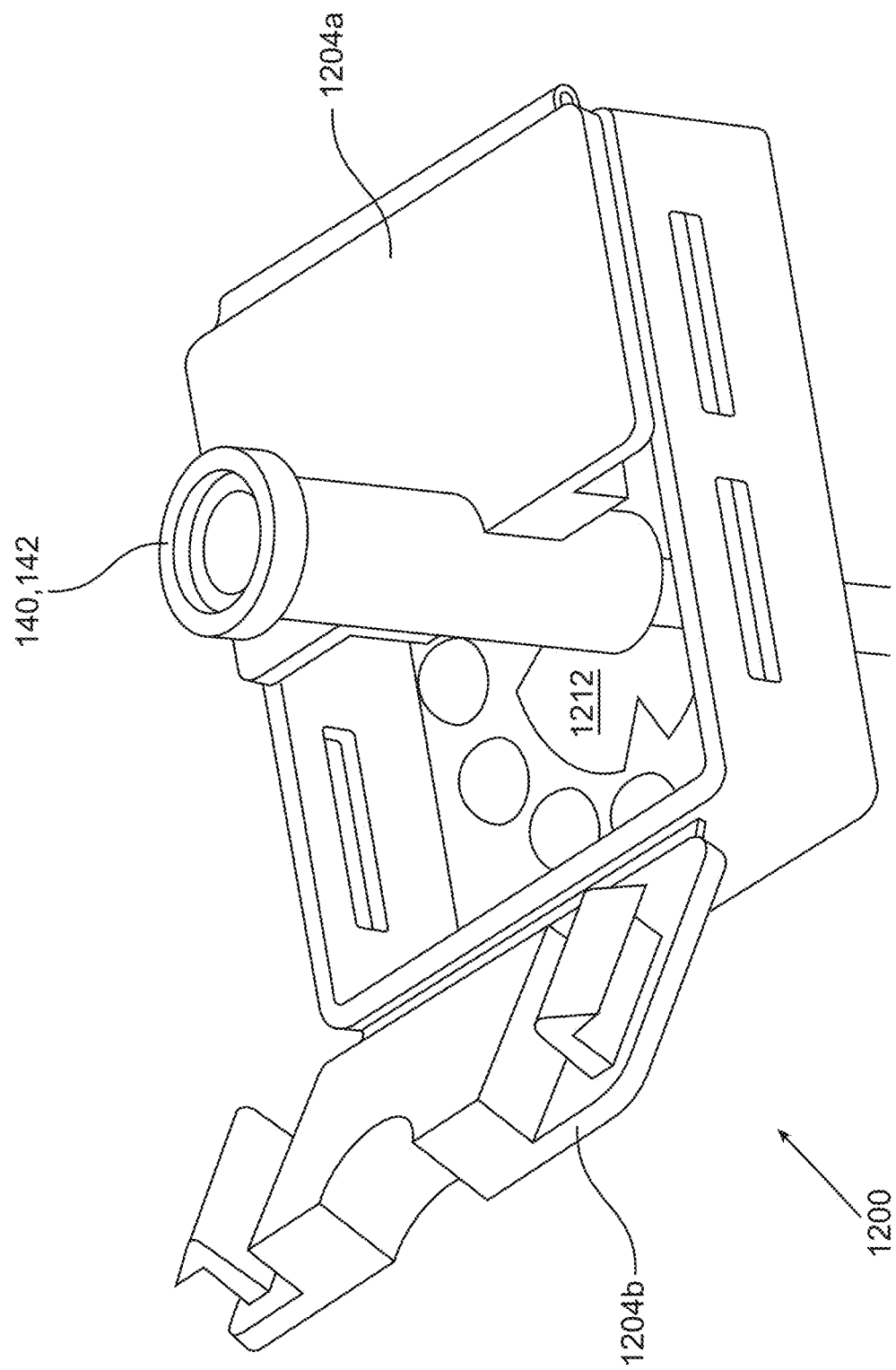
FIG. 13 illustrates the catheter securing assembly as shown in FIG. 12 with one locking door in a locked position according to aspects of the embodiments.
Figure 14:
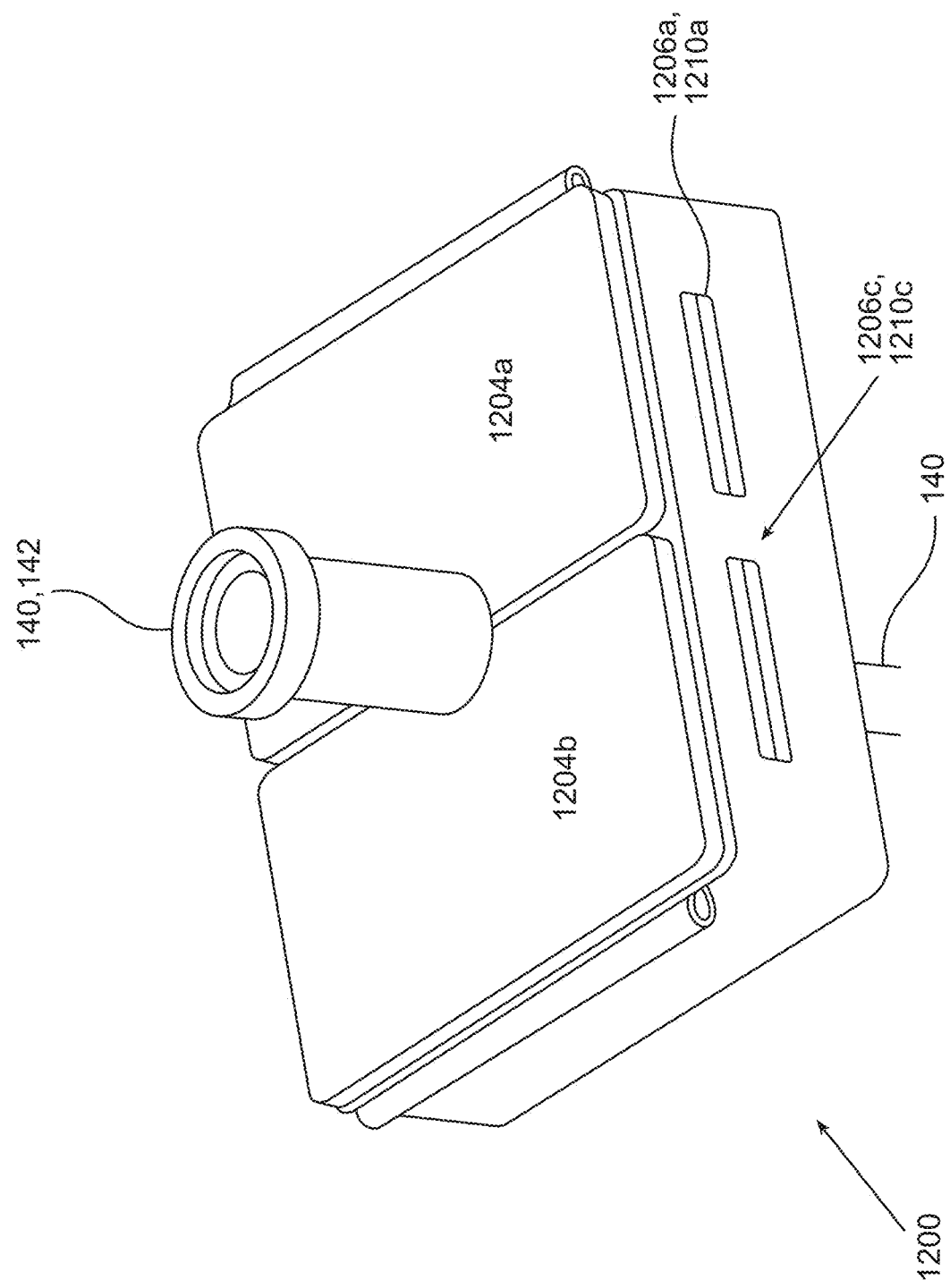
FIG. 14 illustrates the catheter securing assembly as shown in FIG. 12 with two locking doors in a locked position according to aspects of the embodiments.
Figure 15A:
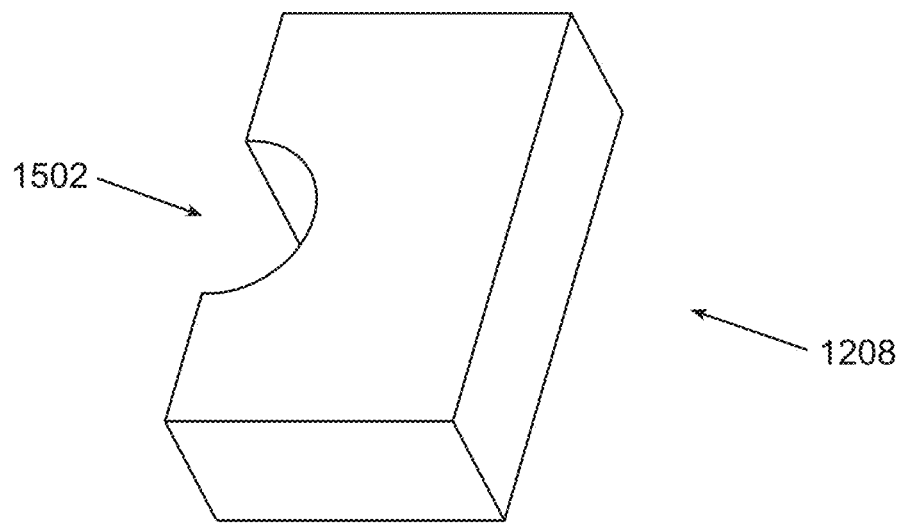
FIGS. 15A-15C illustrate several views of a retention pad for use in the catheter securing assembly of FIG. 12 according to aspects of the embodiments.
Figure 15B:
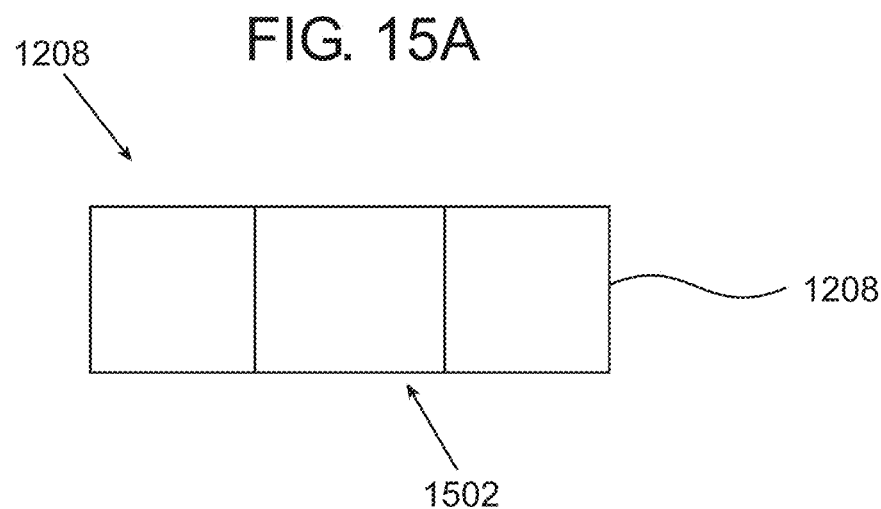
Figure 15C:
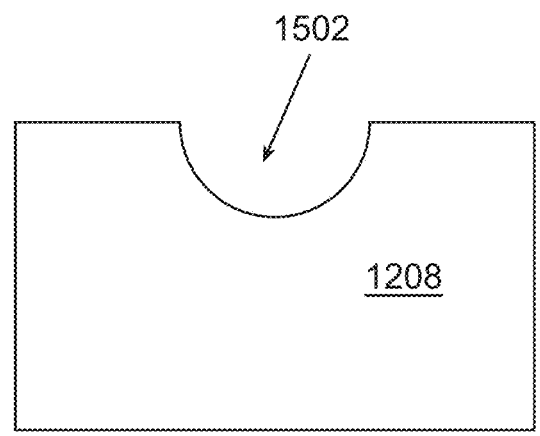
Figure 16:
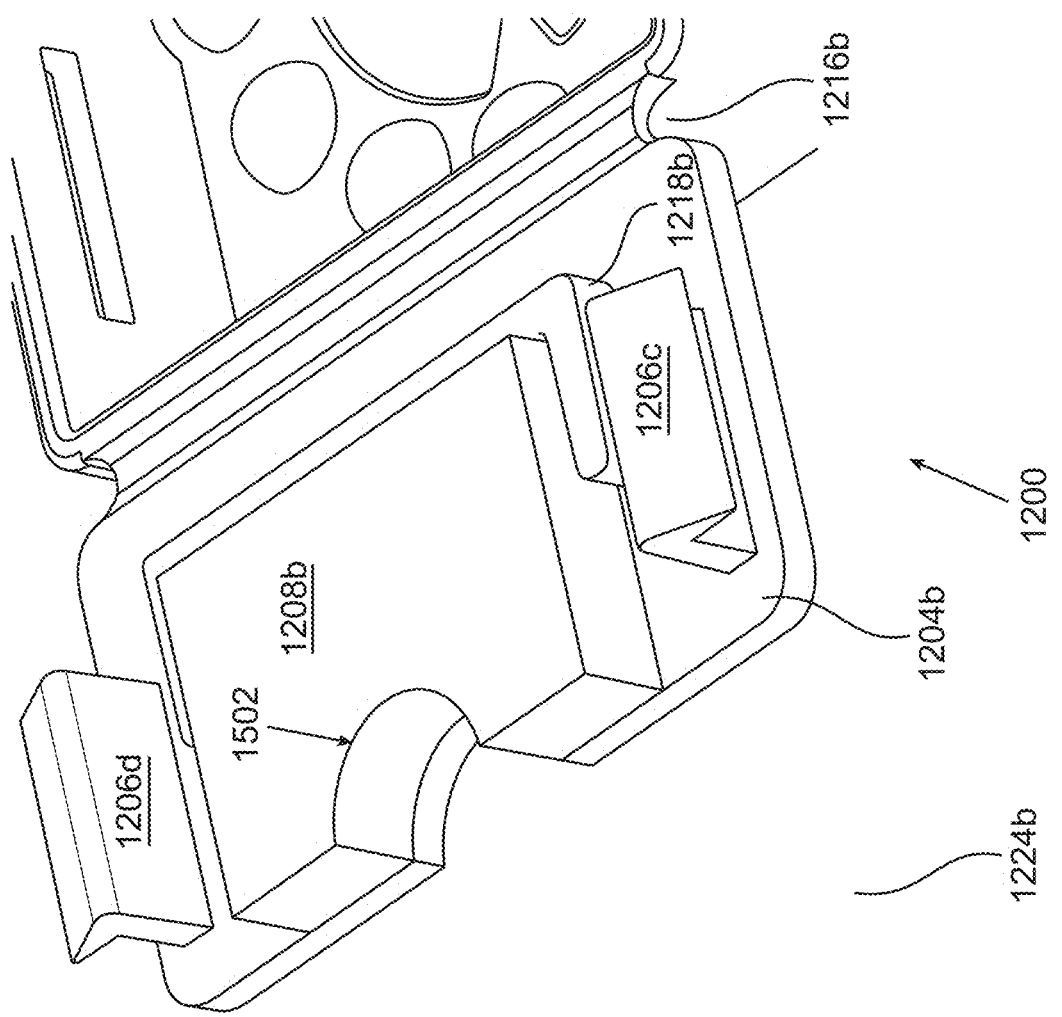
FIG. 16 illustrates a close-up top perspective view of a locking door of the catheter securing assembly of FIG. 12 with the retention pad within the locking door according to aspects of the embodiments.
Figure 19A:
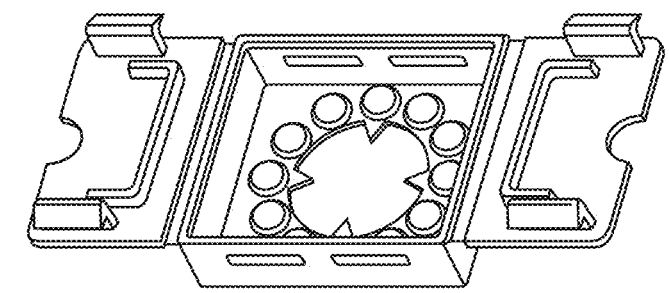
FIGS. 19A-E illustrates several views of a fourth embodiment of a catheter securing assembly or components thereof according to further aspects of the embodiments.
Figure 19B:
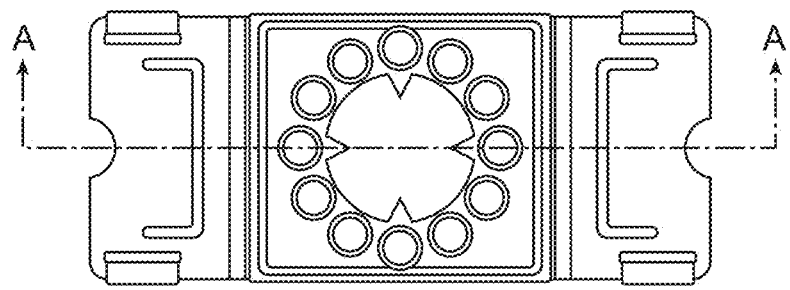
Figure 19C:
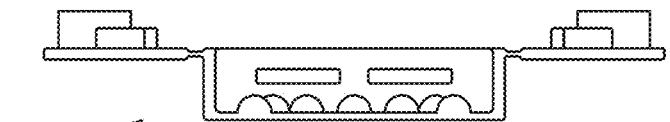
Figure 19D:
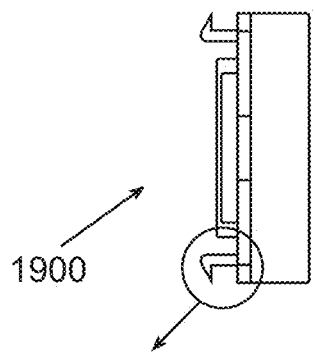
Figure 19E:
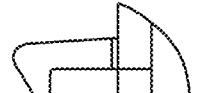

Attention is directed to FIGS. 12-16. FIG. 12 illustrates a top perspective view of a catheter securing mechanism 1200 when opened according to further aspects of the embodiments; FIG. 13 illustrates the catheter securing mechanism as shown in FIG. 12 with one locking door in a locked position according to aspects of the embodiments; FIG. 14 illustrates the catheter securing mechanism as shown in FIG. 12 with two locking doors in a locked position according to aspects of the embodiments; FIGS. 15A-15C illustrate several views of a retention pad for use in the catheter system of FIG. 12 according to aspects of the embodiments; and FIG. 16 illustrates a close-up top perspective view of a locking door of the catheter system of FIG. 12 with the retention pad within the locking door according to aspects of the embodiments.

According to further aspects of the embodiments, catheter securing assembly 1200 comprises frame 1202, sides 1222, first and second locking doors 1204*a,b*, first-fourth locking tabs 1206*a-d*, first and second catheter retention pad (retention pad) 1208*a,b*, first-fourth locking tab receptacles 1210*a-d*, catheter/catheter-hub (hub) pass through hole 1212 (for the purpose of this portion of the discussion, reference shall only be made to catheter hub (hub) 142, although, according to further aspects of the embodiments, use of catheter 140 can be readily accomplished; however, in fulfillment of the dual purposes of clarity and brevity, reference to catheter 140 has been omitted in this portion of the discussion), nubs 1214, first and second hinges 1216*a,b*, and first and second pad holding ridge 1218.

Catheter securing assembly 1200 is generally cubic shaped, with base 1220 and four side 1222 as shown in FIG. 12. Generally centrally located in base 1220 is hub pass through hole 1212. In the embodiment of FIG. 12, hub pass through hole 1212 is generally clover-leaf in configuration, although hub pass through hole has an overall circular or round shape to it as well. Surrounding hub pass through hole 1212 are a plurality of nubs 1214: in the embodiment shown in FIG. 12 these number 12. Nubs 1214 are discussed in greater detail below. Located on sides 1222*b,d*, at the top-most portion, are locking doors 1204*a,b*, respectively, connected to sides 1222 by a respective hinge 1216*a,b*; hinges 1216*a,b* can be formed in the injection molding process by merely making the respective area a bit thinner than the balance of catheter securing mechanism 1200. Those of skill in the art of plastic injection molding can appreciate the manner in which such hinge areas can be fabricated from the molding process, and therefore a detailed description of the same has been omitted in fulfillment of the dual purposes of clarity and brevity.

Located on opposing sides 1222*a,c*, are a plurality of locking tab receptacles 1210*a-d*, which are appropriately sized, shaped, and located to interface with locking tabs 1206*a-d* that are part of locking doors 1204*a,b*. Locking doors 1204*a,b* are discussed in greater detail below. On an interior surface of locking doors 1204*a*, 1204*b* are pad holding ridges 1218*a,b*, which are shown in and discussed in greater detail below in regard to FIG. 16; catheter hub retention pads (retention pads) 1208 are shown in, and discussed in greater detail below in regard to FIGS. 15A-C.

According to aspects of the embodiments, and as briefly discussed above, catheter securing assembly 1200 can take the place of first and second grommets 115, 120 in assembly 100 for securing a catheter 140 (or hub 142) in base 105, but the opening would be shaped to match that of catheter securing assembly 1200, which in this non-limiting case is substantially square. According to further aspects of the embodiments, none of assemblies 1200, 1700, 1800, 1900, 2000, 2400, and 2600 are limited to square or rectangular footprints, as other shapes are possible. Thus, catheter securing assembly 1200 would further include medical adhesive 130 and be situated on patient 135 as shown in FIG. 2. In addition, similar to the arrangement shown in FIG. 5, catheter securing assembly 1200 in concert with base 105 could implement clips 145, 145' to secure catheter 140 when attached to hub 142 according to further aspects of the embodiments.

FIG. 12 illustrates a top perspective view of catheter securing mechanism 1200 when opened according to further aspects of the embodiments. In FIG. 12, it can be seen that first and second locking doors 1204*a,b* are open and this replicates the manner in which catheter securing assembly 1200 would be placed or located over hub 142 that has already been placed in a body of patient 135. In each of locking doors 1204*a*, 1204*b* are retention pads 1208*a,b*, respectively. Each of locking doors 1204*a,b*, while being configured, sized and shaped to provide a substantially enclosing fixture for catheter securing mechanism 1200, further include door hub pass through hole 1224*a,b*, respectively, which, when locking doors 1204*a,b* are in a closed position, provide a through hole for hub 142. As those of skill in the art can appreciate, door hub pass through hole 1224*a,b* according to aspects of the embodiments can be made to be of a slightly larger diameter than that of hub 142; however, retention pads 1208*a,b*, which fit within and are substantially retained by respective pad holding ridges 1218*a,b* of locking doors 1204*a,b* also include respective pad holes 1502*a,b* (as shown in FIGS. 15A-15C), which can be made to have a slightly smaller diameter than that of hub 142 in order to provide a frictional engagement with hub 142 to substantially secure hub 142 in place.

FIG. 13 illustrates catheter securing assembly 1200 with a first locking door 1204 in a locked position according to aspects of the embodiments, wherein retention pad 1208*a* is in contact with hub 142, and FIG. 14 illustrates catheter securing mechanism 1200 with first and second locking doors 1204*a,b* in a locked position, such that both first and second retention pads 1208*a,b* are in contact with hub 142 according to aspects of the embodiments.

FIGS. 15A-15C illustrate several views of retention pad 1208, and FIG. 16 illustrates a close-up top perspective view of second locking door 1204*b* with retention pad 1208*b* located therein according to aspects of the embodiments. Retention pad 1208 can retained by pad holding ridge 1218 either by frictional engagement (i.e., being made of such dimensions that it is compressed into and retained by holding ridge 1218), or can be retained by a glue or some other similar securing means (e.g., ultra-sonic welding, among other methods). In addition, as briefly discussed above, catheter securing assembly 1200 further comprises a plurality of nubs 1214 on an interior surface of base 1220. According to aspects of the embodiments, and as shown in one or more of FIGS. 12-26, there are 12 nubs 1214, though that number is not to be taken in a limiting manner. Each of nubs 1214 impacts a bottom surface of both retention pads 1208*a,b*, forcing them up against respective locking doors 1204*a,b*, each other, and hub 142, thus providing additional frictional retention force between catheter securing assembly 1200 and hub 142.

According to further aspects of the embodiments, retention pads 1208*a,b* can be fabricated from silicon rubber to provide frictional engagement with hubs 142 that are generally made up of a plastic.

According to further aspects of the embodiments, retention pads 1208*a,b* within catheter securing assembly 1200 provides superior adhesion for high traffic/disturbance areas on a patient's body.

According to further aspects of the embodiments, retention pads 1208*a,b* within catheter securing assembly 1200 helps prevent kinking of a Turkel-type hub 142, and further substantially prevents 14 gauge needle decompression catheters 140 from folding over and being useless/ineffective for treatment.

According to further aspects of the embodiments, catheter pass through hole 1212 of catheter securing assembly 1200 allows for insertion point guidance and sterilization.

According to further aspects of the embodiments, catheter securing assembly 1200 is quicker than current methods for securing needle decompression catheters and saves vital pre-hospital patient care time, and makes caregivers job easier, by requiring only one person to secure the assembly 1200.

According to further aspects of the embodiments, catheter securing assembly 1200 allows for specific depth placement and retention at said depth. Burying a Turkel-type catheter is no longer needed so the caregiver can substantially avoid harming internal tissues/organs.

Attention is directed again to FIGS. 12-14 and 16. In each of these Figures, one or more of locking tabs 1206 and locking tab receptables 1210 can be seen. According to aspects of the embodiments, locking tabs 1206 and locking tab receptacles 1210 are sized, shaped, and arranged such that a compressive fit is obtained for locking doors 1204*a,b* and subsequently retention pads 1208*a,b*. According to further aspects of the embodiments, catheter securing assembly 1200 is a one-time use device, Thus, locking tabs 1206 and receptacles 1210 are sized, shaped, and configured to make it relatively easy to insert locking tabs 1206 into receptacles 1210, but not to retract them from receptacles 1210.

Figure 22:
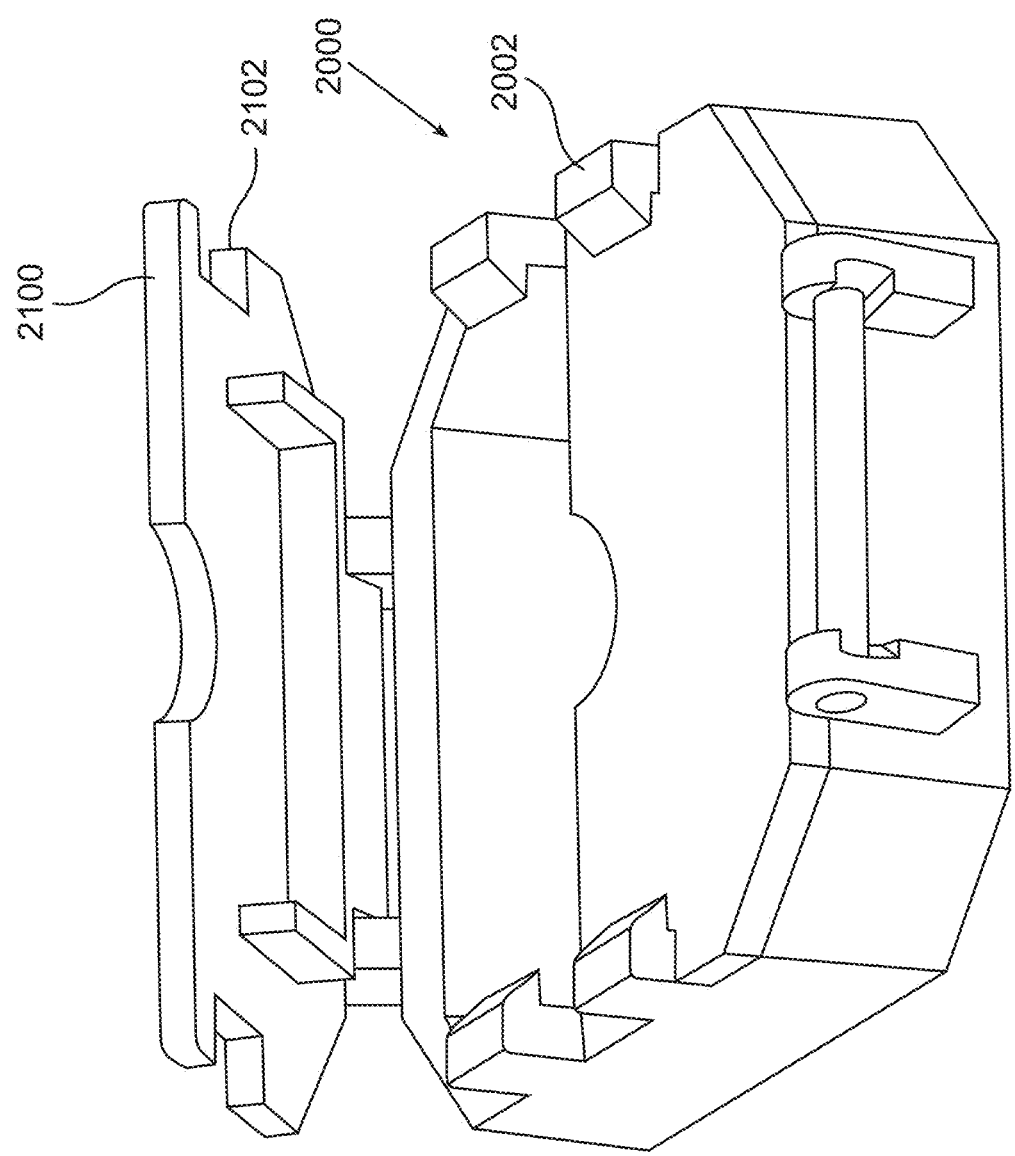
FIG. 22 illustrates a top perspective view of the fifth embodiment of the catheter securing assembly shown in FIGS. 20A-20E according to further aspects of the embodiments.
Figure 23:
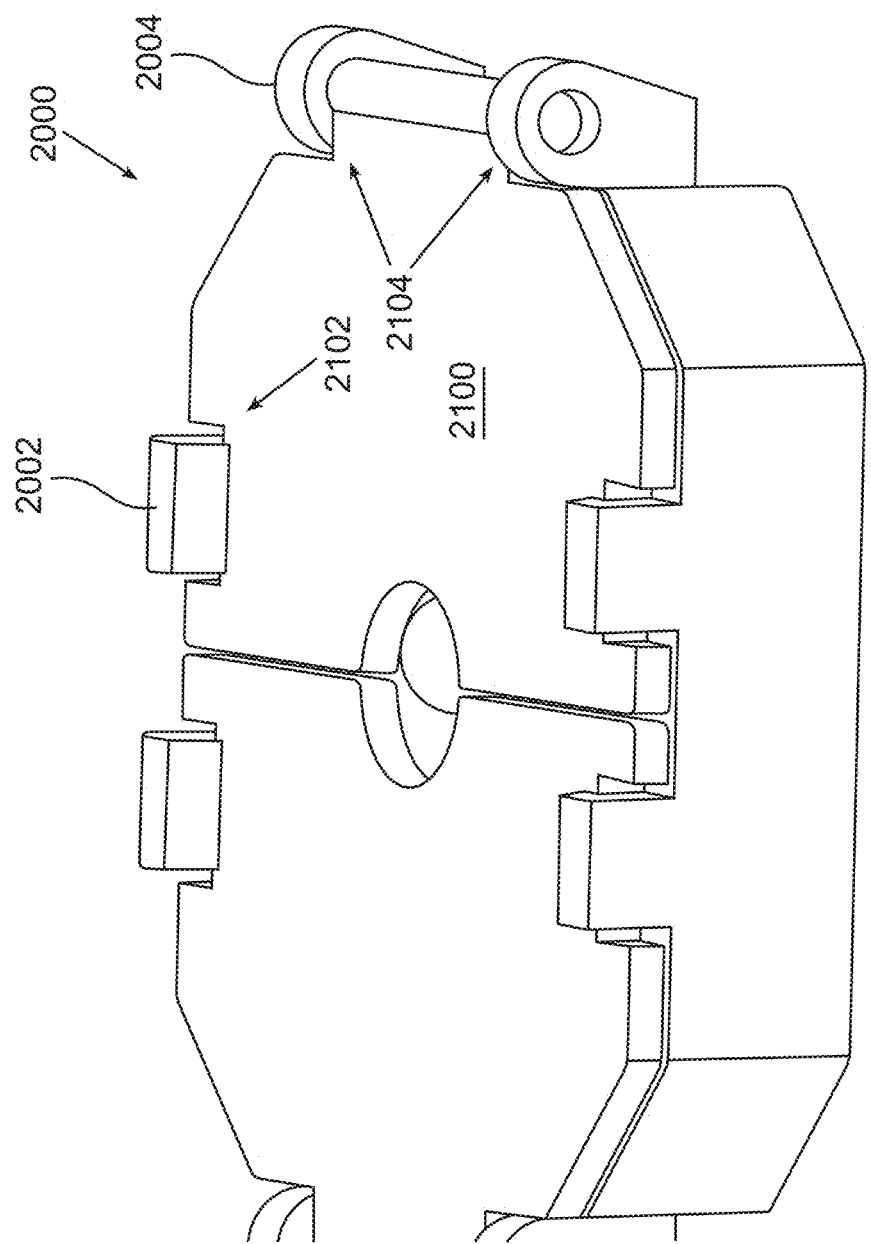
FIG. 23 illustrates a top perspective view of the catheter securing assembly as shown in FIG. 22 when closed according to further aspects of the embodiments.
Figure 24:
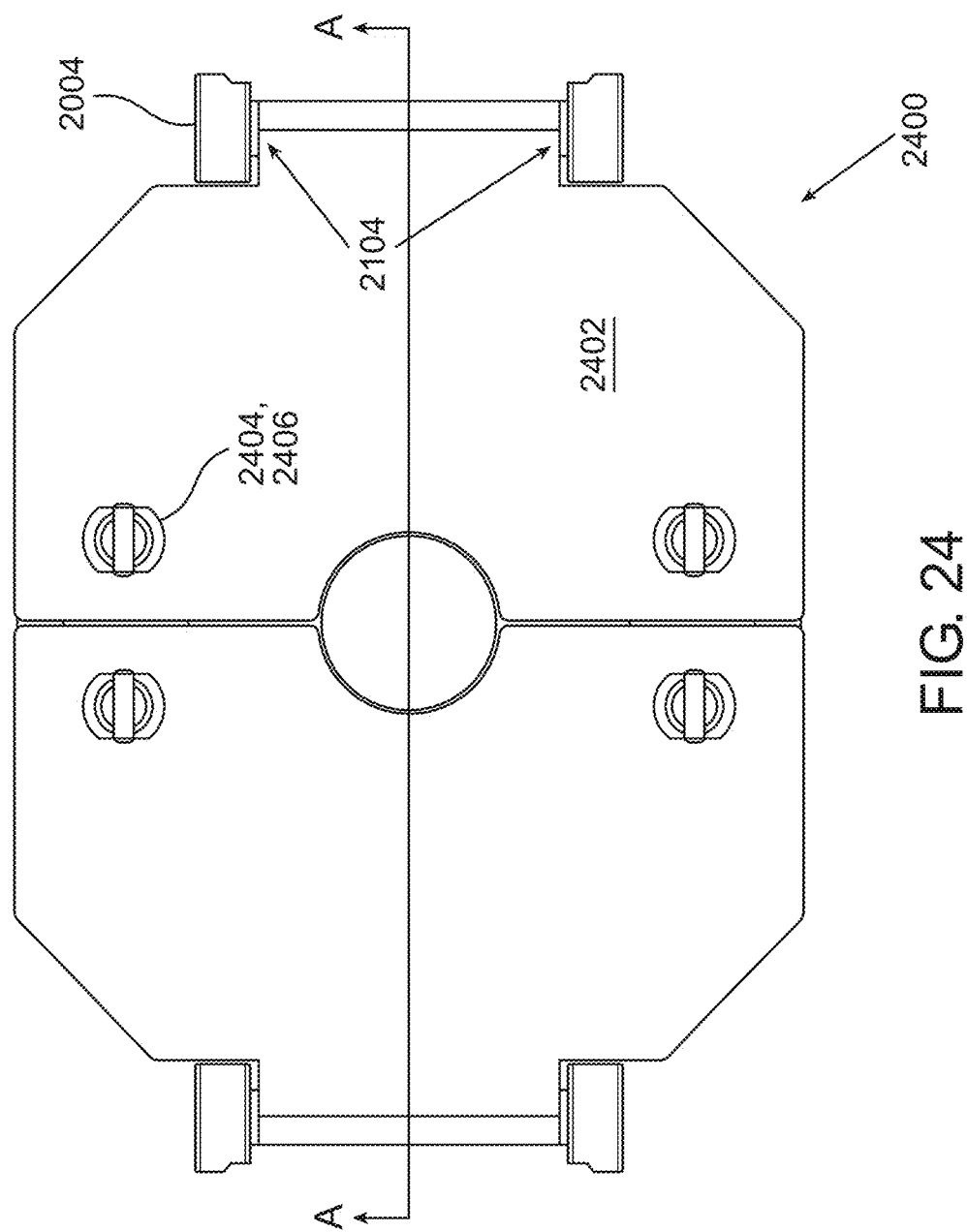
FIG. 24 illustrates a top view of a sixth embodiment of a catheter securing assembly according to further aspects of the embodiments.
Figure 25:
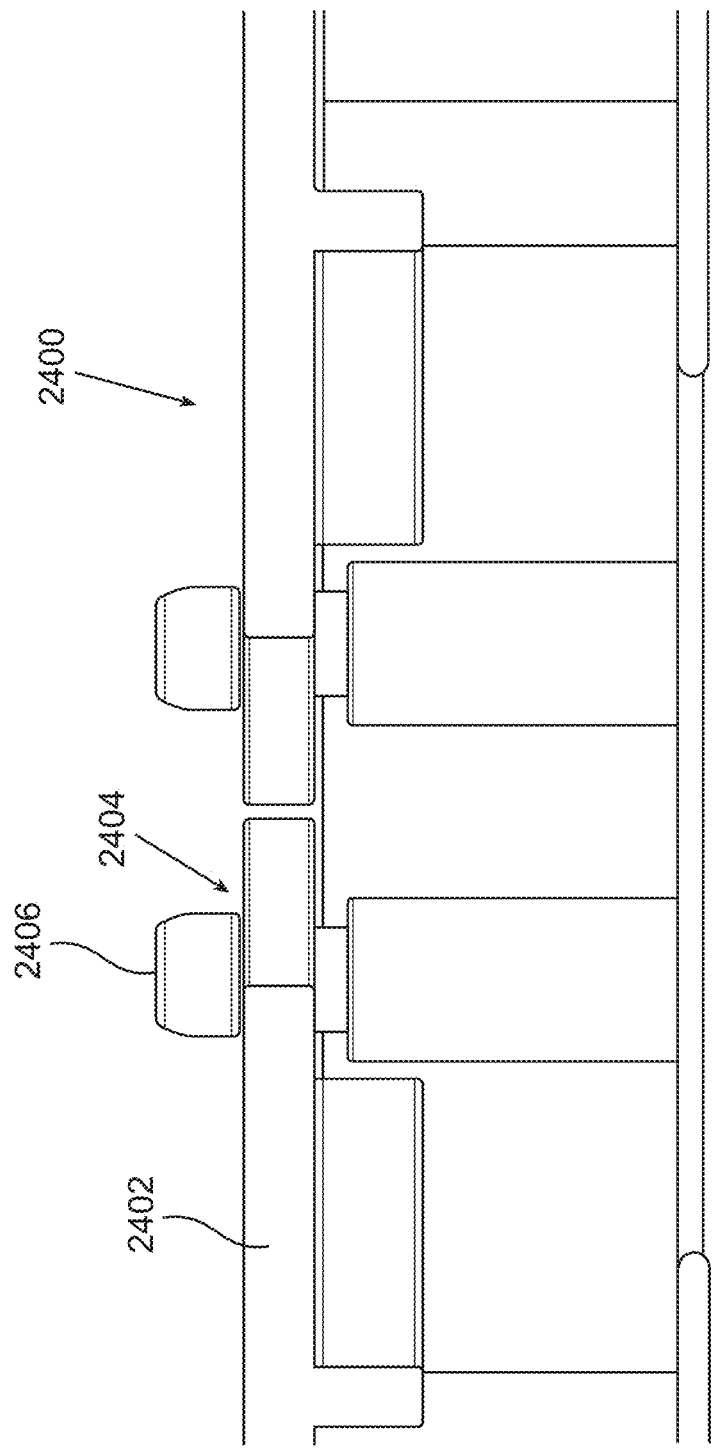
FIG. 25 illustrates a cut away view of the catheter securing assembly of FIG. 24 along line A-A.
Figure 26:
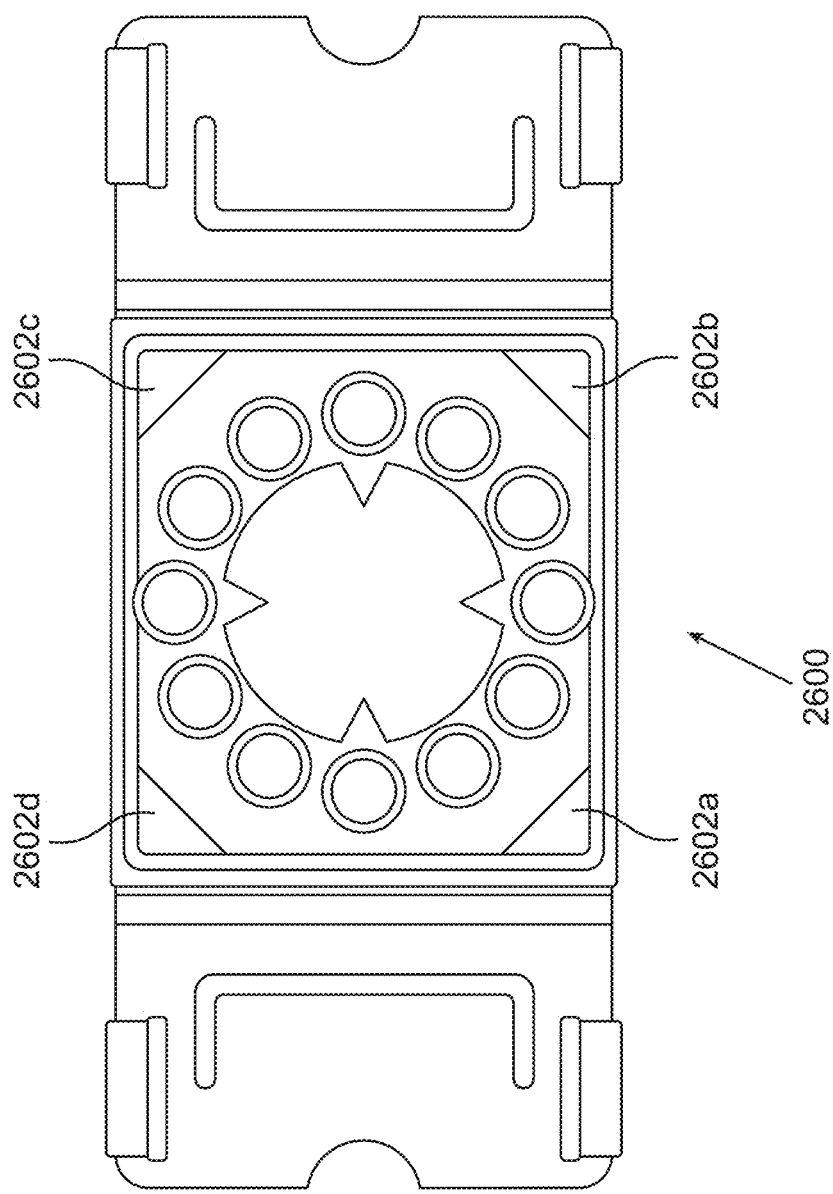
FIG. 26 illustrates a top perspective view of a seventh embodiment of a catheter securing assembly according to further aspects of the embodiments.
Figure 27:
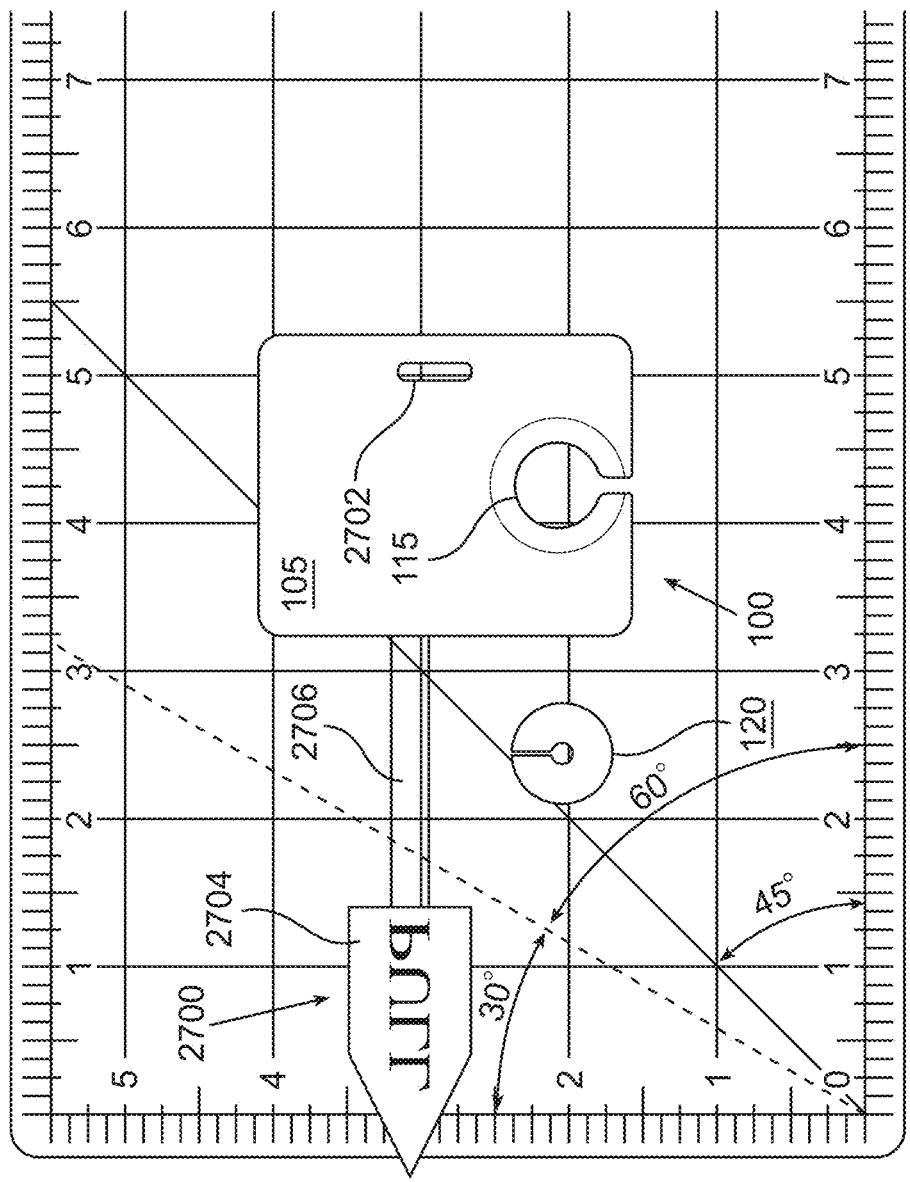
FIGS. 27-31 illustrate a catheter tube securing assembly according to further aspects of the embodiments.
Figure 28:
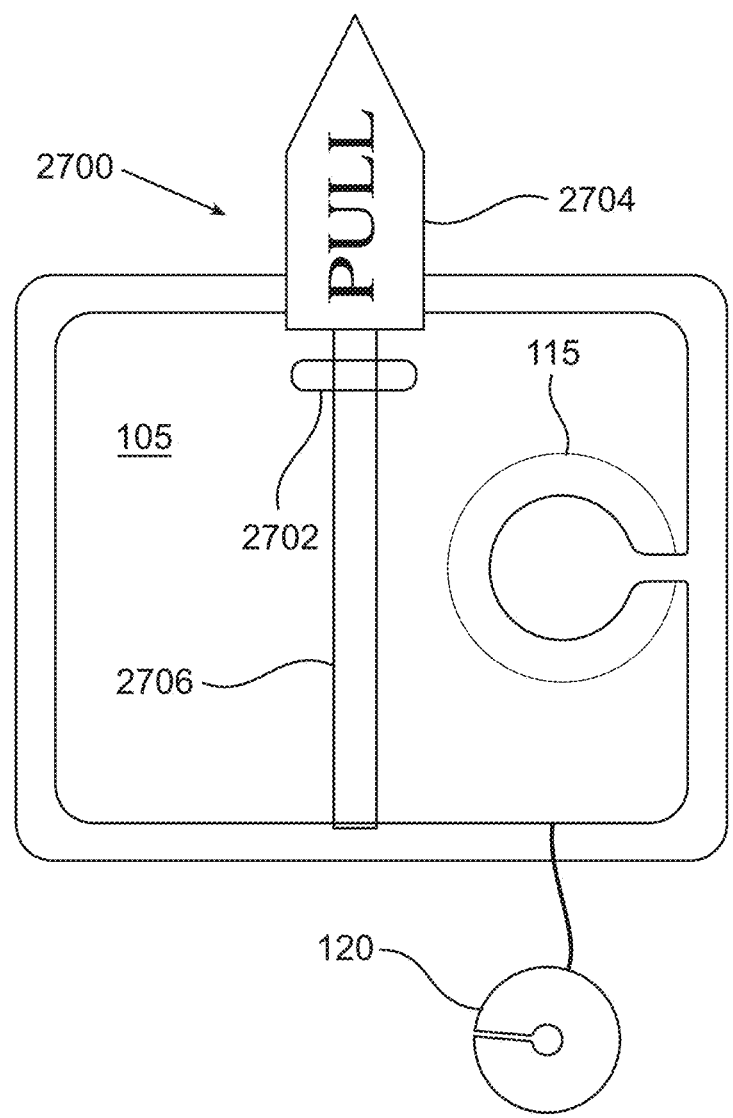

Attention is directed now to FIGS. 17-26. FIGS. 17A-17E illustrates several views of a second embodiment of a catheter securing assembly or components thereof according to further aspects of the embodiments; FIGS. 18A-18E illustrates several views of a third embodiment of a catheter securing assembly or components thereof according to further aspects of the embodiments; FIGS. 19A-E illustrates several views of a fourth embodiment of a catheter securing assembly or components thereof according to further aspects of the embodiments; FIGS. 20A-20E illustrates several views of a fifth embodiment of a catheter securing assembly or components thereof according to further aspects of the embodiments; FIGS. 21A-21C illustrate several views of a locking door for use with the fifth embodiment of the catheter securing assembly shown in FIGS. 20A-20E according to further aspects of the embodiments; FIG. 22 illustrates a top perspective view of the fifth embodiment of the catheter securing assembly shown in FIGS. 20A-20E according to further aspects of the embodiments; FIG. 23 illustrates a top perspective view of the catheter securing assembly as shown in FIG. 22 when closed according to further aspects of the embodiments; FIG. 24 illustrates a top view of a sixth embodiment of a catheter securing assembly according to further aspects of the embodiments; FIG. 25 illustrates a cut away view the catheter securing assembly of FIG. 24 along line A-A; and FIG. 26 illustrates a top perspective view of a seventh embodiment of a catheter securing assembly according to further aspects of the embodiments.

FIGS. 17A-17E illustrates several views of catheter securing assembly 1700 or components thereof according to further aspects of the embodiments. Catheter securing assembly 1700 shown in FIGS. 17A-17E includes many of the same components as catheter securing assembly 1200, but they have not been enumerated or discussed in fulfillment of the dual purposes of clarity and brevity. Catheter securing assembly 1700 includes integrated locking doors that are substantially similar to that of catheter securing assembly 1200 and is in most ways substantially similar to that of catheter securing assembly 1200 but has different dimensions of several components such as increased wall thickness and reduced length of locking tabs.

FIGS. 18A-18E illustrates several views of catheter securing assembly 1800 or components thereof according to further aspects of the embodiments. Catheter securing assembly 1800 shown in FIGS. 18A-18E includes many of the same components as catheter securing assembly 1200, but they have not been enumerated or discussed in fulfillment of the dual purposes of clarity and brevity. Catheter securing assembly 1800 includes integrated locking doors that are substantially similar to that of catheter securing assembly 1200 and 1700 and is in most ways substantially similar to that of catheter securing assembly 1200 and 1700 but has different dimensions of one or more components.

FIGS. 19A-E illustrates several views of catheter securing assembly 1900 or components thereof according to further aspects of the embodiments. Catheter securing assembly 1900 shown in FIGS. 19A-19E includes many of the same components as catheter securing assembly 1200, 1700, and 1800, but they have not been enumerated or discussed in fulfillment of the dual purposes of clarity and brevity. Catheter securing assembly 1900 includes integrated locking doors that are substantially similar to that of catheter securing assembly 1200, 1700, and 1900, and is in most ways substantially similar to that of catheter securing assembly 1200, 1700, and 1800, but has different dimensions of one or more components.

FIGS. 20A-20E illustrates several views of catheter securing assembly 2000 or components thereof according to further aspects of the embodiments; FIGS. 21A-21C illustrate several views of detachable locking door 2100 for use with catheter securing assembly 2000 shown in FIGS. 20A-20E according to further aspects of the embodiments; FIG. 22 illustrates a top perspective view of catheter securing assembly 2000 with one detachable locking door open according to further aspects of the embodiments; and FIG. 23 illustrates a top perspective view of catheter securing assembly 2000 with both detachable locking doors 2100 closed according to further aspects of the embodiments.

Catheter securing assembly 2000 shown in FIGS. 20A-20E includes many of the same components as catheter securing assembly 1200, 1700, 1800, and 1900, but they have not been enumerated or discussed in fulfillment of the dual purposes of clarity and brevity.

According to further aspects of the embodiments, catheter securing assembly 2000, however, includes detachable locking doors 2100 that, while substantially similar in functionality to the locking doors of catheter securing assemblies 1200, 1700, 1800, and 1900, nonetheless include other design changes, such as placement of locking tabs 2002a-d. In catheter securing assembly 2000, locking tabs 2002a-d are located on top of sides 1222a,c, such that detachable locking doors 2100 engage the stationary locking tabs 2002a-d when detachable locking doors 2100 are moved from an open to a closed position. In addition, locking tab receptacles 1210 are not used in catheter securing assembly 2000; instead, locking tab recesses 2102a,b are located on opposite sides of detachable locking door 2100 as shown in FIG. 21A-21C so that they engage with stationary locking tabs 2002a-d when detachable locking doors 2100 are moved to the closed position. Detachable locking door 2100 further comprises hinge protrusions 2104a,b that can be press-fit into respective hinge receptacles 2004 as shown in FIG. 20 in a manner known to those of skill in the art. According to further aspects of the embodiments, catheter securing assembly 2000, while substantially similar in size and shape to the other catheter securing assemblies 1200, 1700, 1800, and 1900, is different in that it comprises an eight sided polygon box, as opposed to the four sided polygon boxes of the other catheter securing assemblies 1200, 1700, 1800, and 1900.

FIG. 24 illustrates a top view of catheter securing assembly 2400 according to further aspects of the embodiments, and FIG. 25 illustrates a cut away view of catheter securing assembly 2400 of FIG. 24 along line A-A.

Catheter securing assembly 2400 shown in FIGS. 24 and 25 includes many of the same components as catheter securing assemblies 1200, 1700, 1800, 1900, and 2000, but they have not been enumerated or discussed in fulfillment of the dual purposes of clarity and brevity. According to further aspects of the embodiments, catheter securing assembly 2400, similar to catheter securing assembly 2000, includes detachable locking doors 2402 that, while substantially similar in functionality to the locking doors of catheter securing assemblies 1200, 1700, 1800, 1900, and 2000, nonetheless include other design changes, such as the use of locking post holes 2404, locking posts 2406, hinge protrusions 2104, and hinge receptacle 2004 (wherein 2004, 2104 are substantially similar in terms of size, shape, and functionality as the similarly enumerated parts of detachable locking doors 2100 shown and described in regard to FIG. 21, among others). According to aspects of the embodiments, locking post hole 2404 is of such shape and size that it accepts a press fit of locking post 2406 in a manner that is known to those of skill in the art (see, FIG. 25). As with locking tabs 1206 and locking tab receptacles 1210, locking posts 2406 and locking post holes 2406 are designed to be substantially press fit together just one time only, as catheter securing assembly 2400, like the other catheter securing assemblies discussed and described herein, are single use devices. According to further aspects of the embodiments, catheter securing assembly 2400, while substantially similar in size and shape to the other catheter securing assemblies 1200, 1700, 1800, and 1900, is different in that it comprises an eight sided polygon box (substantially similar to that of catheter securing assembly 2000), as opposed to the four sided polygon boxes of the other catheter securing assemblies 1200, 1700, 1800, and 1900.

FIG. 26 illustrates a top perspective view of catheter securing assembly 2600 according to further aspects of the embodiments. Catheter securing assembly 2600 is substantially similar in size, shape, configuration and functionality as the other catheter securing assemblies 1200, 1700, 1800, 1900, 2000, and 2400 described herein, with the differences and similarities apparent from the drawing figure; nonetheless, one additional feature shown in catheter securing assembly 2600 are triangle supporting structures 2602a-d. Triangle supporting structures 2602a-d provide substantial mechanical support for sides 1222, and as such can be included in one or more of the described catheter securing assemblies 1200, 1700, 1800, 1900, 2000, and 2400 described herein.

Attention is now directed towards FIGS. 27-31, which illustrates catheter tube securing assembly 2700 implemented with catheter securing assembly 100 according to aspects of the embodiments. As described above, catheter securing assemblies 100, 1200, 1700, 1800, 1900, 2000, 2400, and 2600 can be used to secure catheter 140 and/or hub 142 just as it leaves patient 135; however, according to further aspects of the embodiments, a further inventive apparatus can be used in concert therewith to further secure catheter 140 or the catheter tube that leaves hub 142; this is shown in detail in regard to FIG. 31, wherein catheter securing assembly 100 is affixed to patient 135 and catheter tube securing assembly 2700 affixes tube 3102 to base 105 which is affixed to patient 135.

Figure 29:
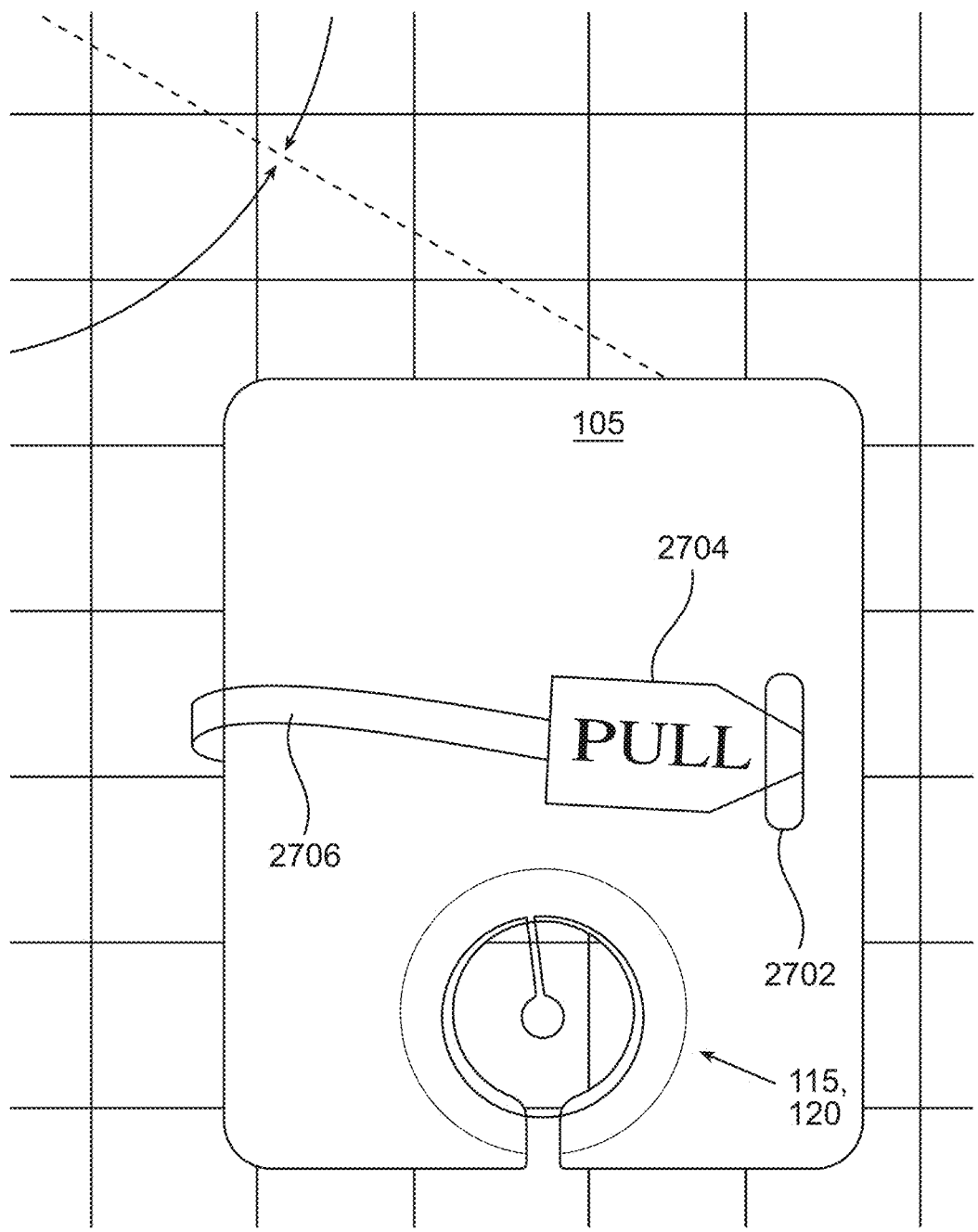
Figure 30:
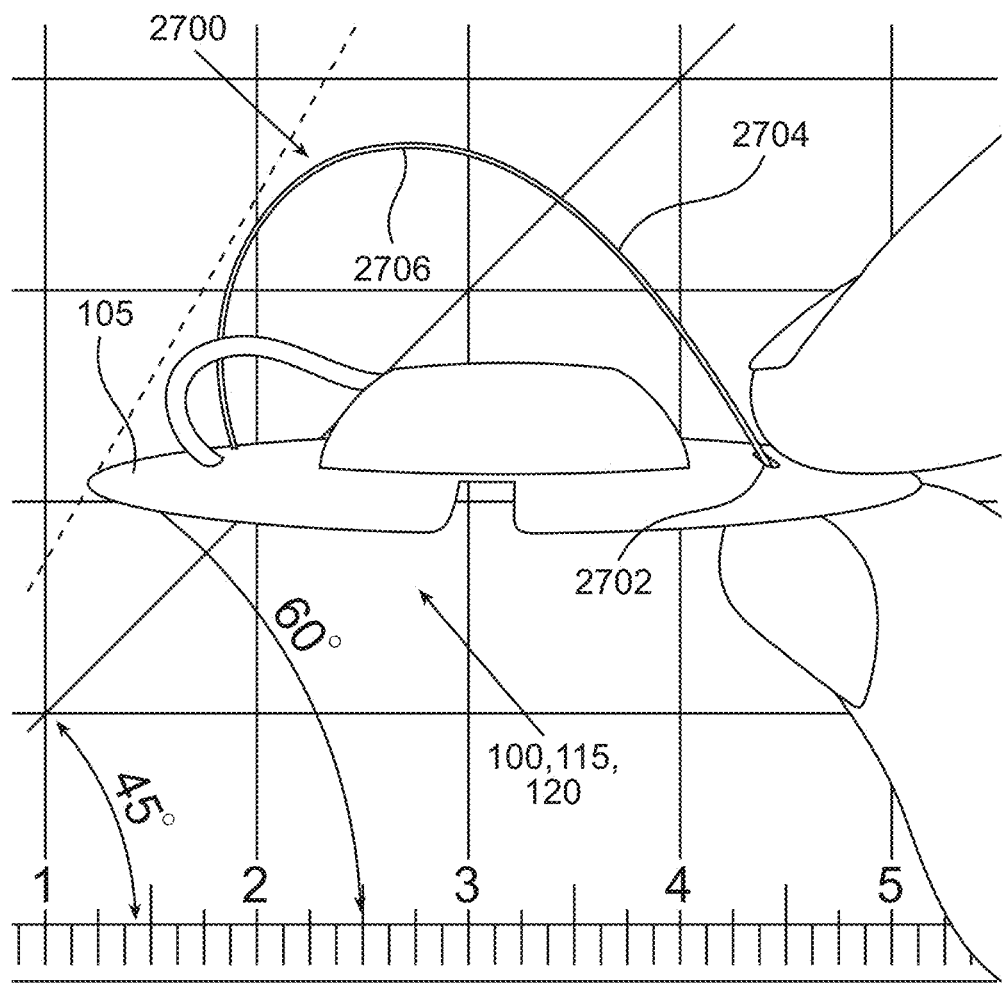
Figure 31:
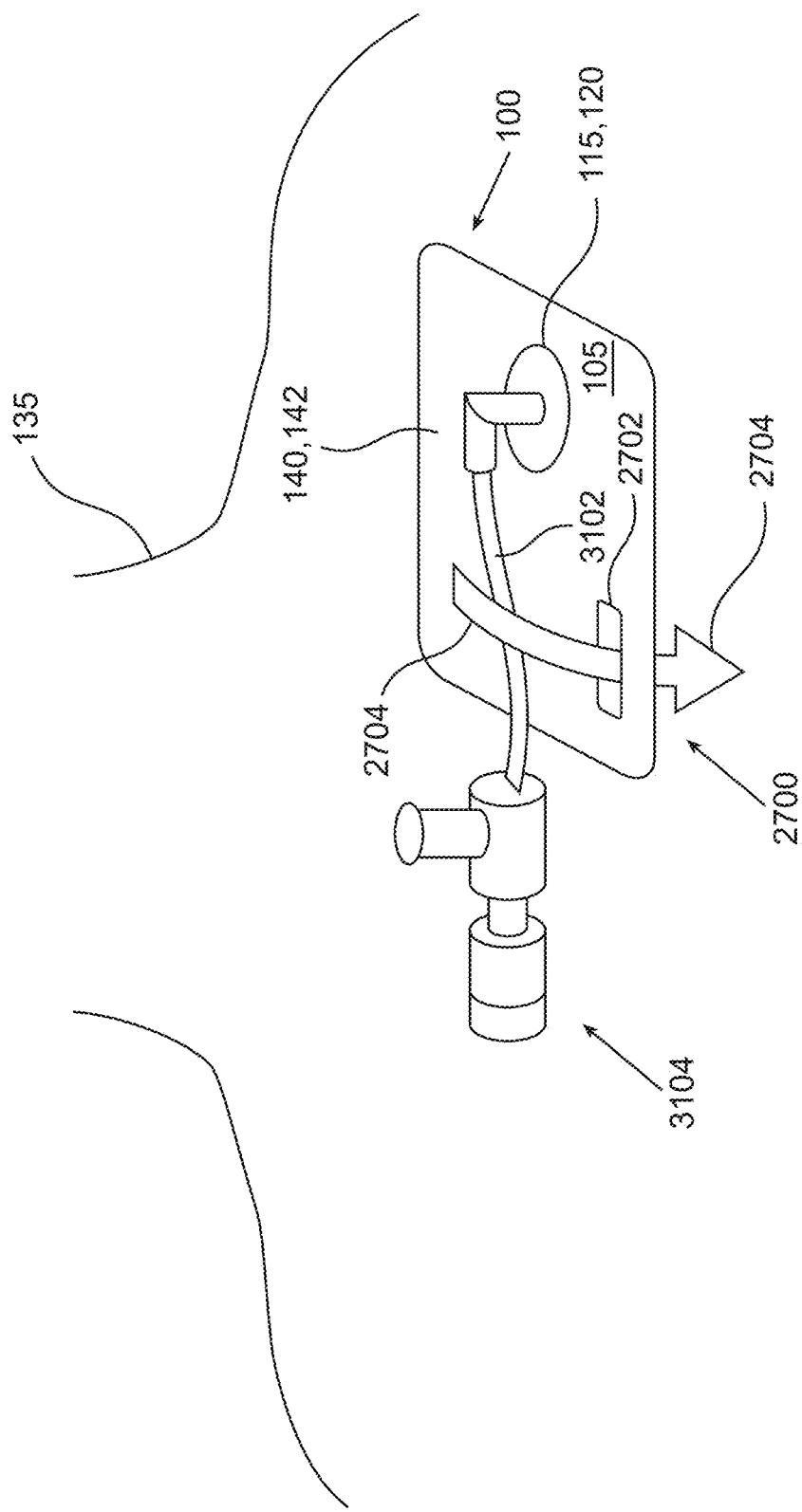

Referring now to FIGS. 27-30, catheter tube securing assembly 2700 comprises securing tab hole 2702, securing tab head 2704, and securing tab body 2706. Catheter tube securing assembly 2700 can be fabricated from the same material as the catheter securing assemblies, or different materials, in the same injection molded process, or in a separate process and then affixed to base 105 using glue, mechanical attachment means, or another process such as ultrasonic welding, and the like, as those of skill in the art can appreciate. Securing tab body 2706 is made of an appropriate length to extend over catheter tube 3102, and head 2704 fits in a one-way fashion through hole 2702, as shown in FIGS. 29-31. According to further aspects of the embodiments, body 2706 can be of different lengths for different uses. In the embodiment shown in FIG. 31, catheter tube securing assembly 2700 secures tube 3102 in such a manner that the catheter hub assembly does not need to be replaced for the duration of use by the patient, as a new tube for different liquids can be inserted into opening 3104 in a manner known to those of skill in the art.

Discussed above in regard to one or more of the Figures, reference has been made to one or more dimensions, which can include one or more of angles, lengths, weights, time, temperature, among others. Those of skill in the art can appreciate that although examples of dimensions are provided, these should not be taken in a limiting manner; that is, the aspects of the embodiments are not to be construed as defined or limited by the specific example of the dimensions shown and discussed, but instead are provided merely for illustrating an example of what a device that incorporates the aspects of the embodiments could, in a non-limiting manner, look like. Furthermore, as those of skill in the art can appreciate, since the aspects of the embodiments are directed towards a physical object, with dimensional characteristics, all of the parts will have various dimensions, some of which are not shown in fulfillment of the dual purposes of clarity and brevity. According to still further aspects of the embodiments, some of these objects will have dimensional characteristics that lend themselves to aesthetic aspects; in fulfillment of the dual purposes of clarity and brevity, dimensions in this regard have also been omitted. Therefore, as the aspects of the embodiments are directed towards a catheter securing assembly, it is to be understood that the dimensions of the different objects, some dimensions shown, some dimensions not shown, will be understood by those of skill in the art.

TABLE 1

Different Types of Catheters and Their Medical Purpose.

| Type of Catheter | Purpose |
| --- | --- |
| Central venous catheter (CVC) | Central line access |
| Turkel catheter | Centesis (fluid drain) |
| Tenckhoff | Ascites drain with on/off switch |
| Hemodialysis catheter | Dialysis; requires two lumen |
| Hickman line | Chemotherapy (also dialysis and central) |
| Groshong line | Three-way valve for central line |
| Quinton catheter | Temporary hemodialysis (untunneled) |
| Huber needle | Chemotherapy |
| Percutaneous endoscopic gastronomy (PEG) | Feeding tube |
| Peripheral insertion central catheter (PICC) | Peripheral insertion |
| Intrauterine pressure catheter (IUPC) | Uterus pressure during contractions |
| Pulmonary artery catheter (PAC) | Swan-Ganz; large vein |
| Suprapubic cystotomy | Bladder drainage (laproscopic) |
| Ports (surgically installed with tunneling) | Insulin and chemotherapy infusion |
| Fogarty embolectomy | Balloon inflates to remove clot |
| Foley catheter | Bladder drainage (urethra) |

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

The invention claimed is:

1. An apparatus for securing a medical device to a patient during a medical procedure, the apparatus comprising:
   a base having a top portion, a bottom portion, and an aperture located on the bottom portion, and wherein the base is configured to be affixed to a patient via the bottom portion; and
   a medical device securing assembly configured to be secured within the aperture in the base,
      the medical device securing assembly comprising a substantially cubic enclosure, a pair of closable doors, and a retention pad secured to an underside of each of the pair of closable doors, and wherein
      the medical device securing assembly is further configured to attach the medical device to the base to hold the medical device in place during the medical procedure,
   wherein approximately 1/3 of the bottom portion of the base includes micro-suction adhesive material with a seating hole for the medical device, and
   wherein the bottom portion of the base is configured to be secured to the patient via an adhesive pad, the adhesive pad occupying approximately 2/3 of a surface area of the bottom portion of the base.

2. The apparatus of claim 1, wherein the adhesive pad comprises via adhesive, micro-suction, glue and combinations thereof.

3. The apparatus of claim 1, wherein the medical device is selected from a group consisting of a needle decompression catheter for chest decompression, a central venous catheter, Turkel catheter, Tenckhoff catheter, Hemodialysis catheter, Hickman line, Groshong line, Quinton catheter, Huber needle, percutaneous endoscopic gastronomy feeding tube, peripherally inserted central catheter, intrauterine pressure catheter, pulmonary artery catheter, Swan-Ganz catheter, and suprapubic catheter.

4. The apparatus of claim 1, wherein the medical device intended for insertion into the patient is pre-attached to the apparatus.

5. The apparatus of claim 1, further comprising at least one clip ring and at least one adhesive strip attached to the base adjacent to the medical device securing assembly and extending away from the medical device securing assembly, the at least one clip able to support varying lengths of the medical device.

6. The apparatus of claim 5, wherein the at least one clip ring is slidable on the at least one adhesive strip.

7. The apparatus of claim 1, wherein the base is a rigid body or a flexible base.

8. The apparatus of claim 1 wherein the medical device securing assembly further comprises:
   a plurality of nubs protruding from an inner surface of a base of the medical device securing assembly, each of the plurality of nubs imparting a force on the retention pad when the pair of closable doors are closed, causing the retention pads to frictionally engage the medical device.

9. The apparatus according to claim 1, wherein the medical device securing assembly further comprises:
   a pair of locking tabs located on each of the pair of closable doors; and
   a pair of locking tab receptacles for each of the pair of locking tabs, the locking tab receptacles located on sides of the enclosure, each of the locking tab receptacles configured to accept a respective locking tab such that the closable doors are substantially locked in place.

10. The apparatus according to claim 1 wherein the medical device securing assembly further comprises:
   a retention pad retaining ridge located on an inner surface of each of the pair of closable doors, the retention pad retaining ridges configured to hold the retention pads substantially in place.

11. The apparatus according to claim 10, wherein the retention pads are held in place on the inner surface of the pair of closable doors by one of glue and ultra-sonic welding.

12. The apparatus according to claim 1 wherein the medical device securing assembly further comprises:
   an aperture located through a base of the enclosure such that the medical device can substantially readily pass through the medical device securing assembly.

13. The apparatus according to claim 1, wherein the medical device securing assembly further comprises:
   a pair of hinge receptacles located on two opposing walls of the enclosure; and
   a pair of hinge protrusions located on opposing sides of the pair of closable doors, wherein
      the hinge protrusions are configured to fit within respective hinge receptacles, wherein the pair of closable doors are detachable.

14. The apparatus of claim 1, wherein the enclosure and retention pads are made from rubber, plastic, silicone, and combinations thereof.

15. The apparatus of claim 1, wherein the apparatus is three dimensionally printed and thereby customized to conform to the patient.

16. A method for securing a medical device to a patient during a medical procedure, the method comprising the following steps:
   providing an apparatus according to claim 1;
   securing the base to a skin surface of a patient;
   inserting the medical device into the patient through the aperture in the base and the medical device securing assembly; and
   closing the pair of closable doors such that the medical device is attached to the base.

17. The method of claim 16, wherein the adhesive pad comprises adhesive, micro-suction, glue and combinations thereof.

* * * * *